US008753277B2

(12) United States Patent
McAleavey

(10) Patent No.: US 8,753,277 B2
(45) Date of Patent: Jun. 17, 2014

(54) METHODS AND SYSTEMS FOR SPATIALLY MODULATED ULTRASOUND RADIATION FORCE IMAGING

(75) Inventor: Stephen A. McAleavey, Rochester, NY (US)

(73) Assignee: The University of Rochester, Rochester, NY (US)

( * ) Notice: Subject to any disclaimer, the term of this patent is extended or adjusted under 35 U.S.C. 154(b) by 703 days.

(21) Appl. No.: 12/965,807

(22) Filed: Dec. 10, 2010

(65) Prior Publication Data
US 2011/0184287 A1 Jul. 28, 2011

Related U.S. Application Data

(60) Provisional application No. 61/285,339, filed on Dec. 10, 2009.

(51) Int. Cl.
*A61B 8/00* (2006.01)
(52) U.S. Cl.
USPC ............................... 600/437; 600/459; 601/2
(58) Field of Classification Search
USPC ....................................... 600/437, 459; 601/2
See application file for complete search history.

(56) References Cited

U.S. PATENT DOCUMENTS

| 8,494,791 B2* | 7/2013 | Hazard et al. | 702/56 |
| 2009/0203997 A1* | 8/2009 | Ustuner | 600/443 |
| 2010/0286520 A1* | 11/2010 | Hazard et al. | 600/439 |

OTHER PUBLICATIONS

Carstensen et al., Elastography in the management of liver disease; Ultrasound in Medicine and Biology, 2008, vol. 34, No. 10; pp. 1535-1546.
Sarvazyan et al., Shear wave elasticity imaging: a new ultrasonic technology of medical diagnostics; Ultrasound in Medicine and Biology, Nov. 1998, vol. 24, No. 9; pp. 1419-1435.
Berco et al., Supersonic shear imaging: A new technique for soft tissue elasticity mapping; IEEE Transaction on Ultrasonics, Ferroelectronics and Frequency Control, Apr. 1004, vol. 51, No. 4; pp. 396-409.
Palmeri et al., Quantifying hepatic shear modulus in vivo using acoustic radiation force; Ultrasound in Medicine and Biology, 2008, vol. 34, No. 4; pp. 546-558.
Chen et al., Shear property characterization of viscoelastic media using vibrations induced by ultrasound radiation force; In Proceedings of the IEEE International Ultrasonics Symposium, 2002, vol. 2; pp. 1871-1875.
McAleavey et al., Validation of smurf estimation of shear modulus in hydrogels; Ultrasonic Imaging, 2009, vol. 31; pp. 111-130.
Ophir et al., Correlation artifacts in speed of sound estimation in scattering media; Ultrasound in Medicine and Biology, 1983, vol. 15, No. 4; pp. 341-353.

(Continued)

*Primary Examiner* — Parikha Mehta
(74) *Attorney, Agent, or Firm* — Hodgson Russ LLP

(57) ABSTRACT

Methods for determining the shear modulus of a tissue of an individual are disclosed. In one embodiment, an acoustic pulse is transmitted and a reference echo signal is received. A first push pulse is transmitted at a second location of the individual. A second push pulse is transmitted at a third location of the individual. A series of tracking pulses are transmitted at the first location and a tracking echo signal is received from each tracking pulse. The effect of the first and second push pulses on the tissue is determined through analysis of the tracking echo signals. The shear modulus of the tissue is calculated based on the effect of the push pulses on the tissue. A system for imaging a region of tissue is presented.

18 Claims, 18 Drawing Sheets

(56) References Cited

OTHER PUBLICATIONS

Parker, Ultrasonic attenuation and absorption in liver tissue Ultrasound in Medicine and Biology, 1983, vol. 9, No. 4; pp. 363-369.

McAleavey et al., Shear-modulus estimation by application of spatially modulated impulsive acoustic radiation force; Ultrasonic Imaging, Apr. 2007, vol. 29; pp. 87-104.

Kasai et al., Real-Time Two-Dimensional Blood flow imaging using an autocorrelation technique; IEEE Transactions on Sonics and Ultrasonics, 1985, vol. 32; pp. 458-463.

Zemp et al., Linear System Models for Ultrasonic Imaging: Application to Signal Statistics of Imaging; IEEE Transactions on Ultrasonics, Ferroelectrics and Frequency Control, 2003, vol. 18; pp. 318-329.

Jensen, Field: A Program for Simulating Ultrasound Systems; Medical and Biological Engineering and Computing, 1996, vol. 34; pp. 351-352.

\* cited by examiner

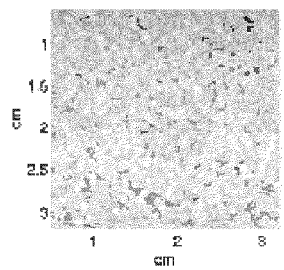 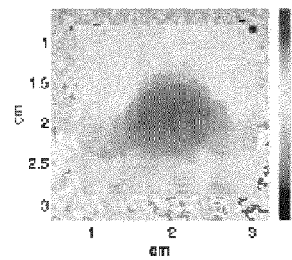 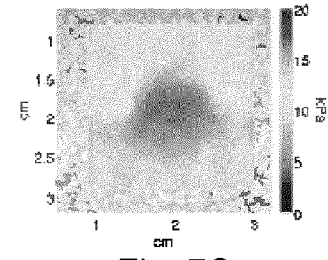
Fig. 7A　　　　　　　Fig. 7B　　　　　　　Fig. 7C
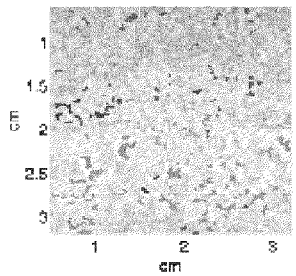 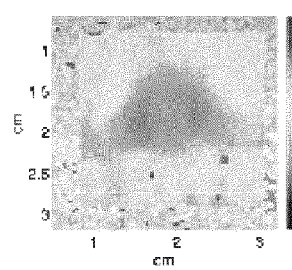 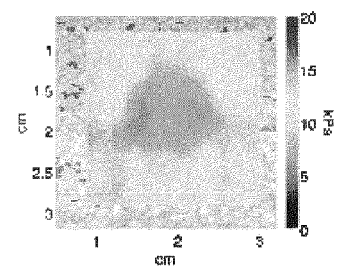
Fig. 7D　　　　　　　Fig. 7E　　　　　　　Fig. 7F
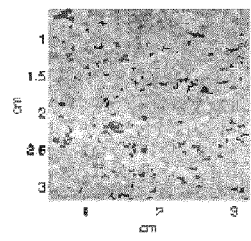 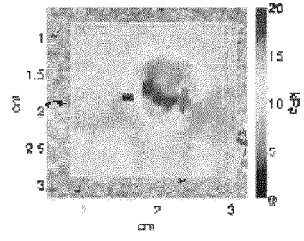 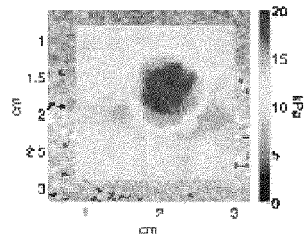
Fig. 7G　　　　　　　Fig. 7H　　　　　　　Fig. 7I

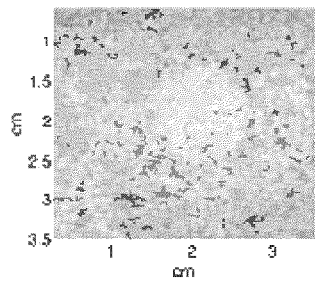 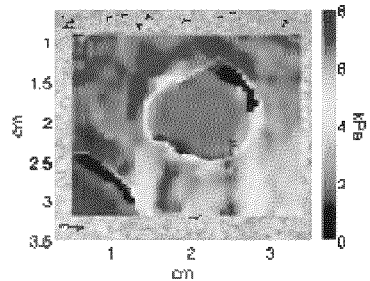
Fig. 10A  Fig. 10B
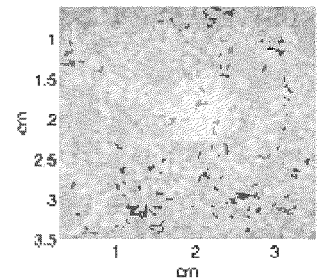 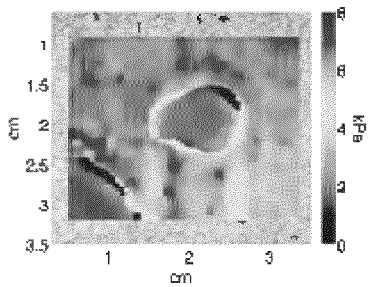
Fig. 10C  Fig. 10D
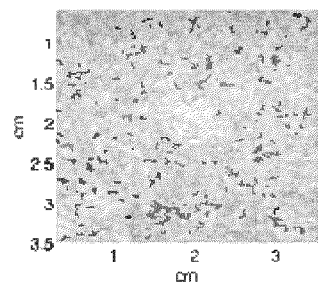 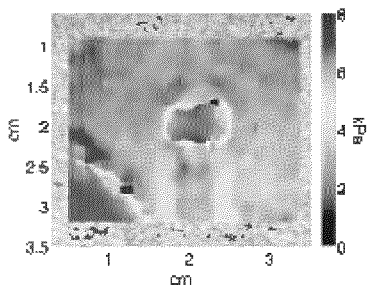
Fig. 10E  Fig. 10F
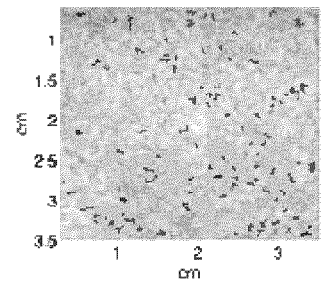 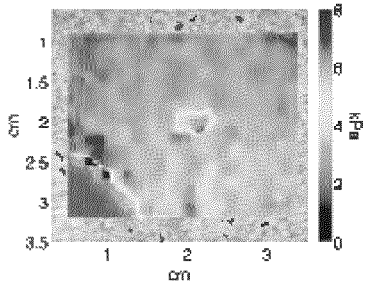
Fig. 10G  Fig. 10H

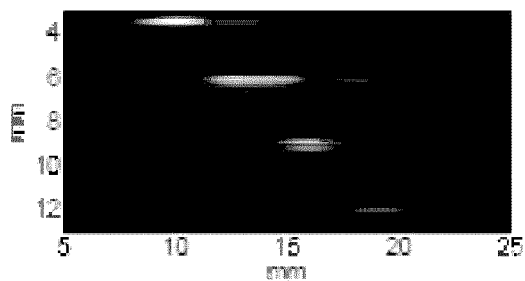 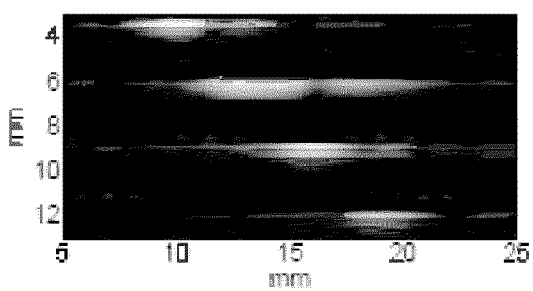
Fig. 17A     Fig. 17B
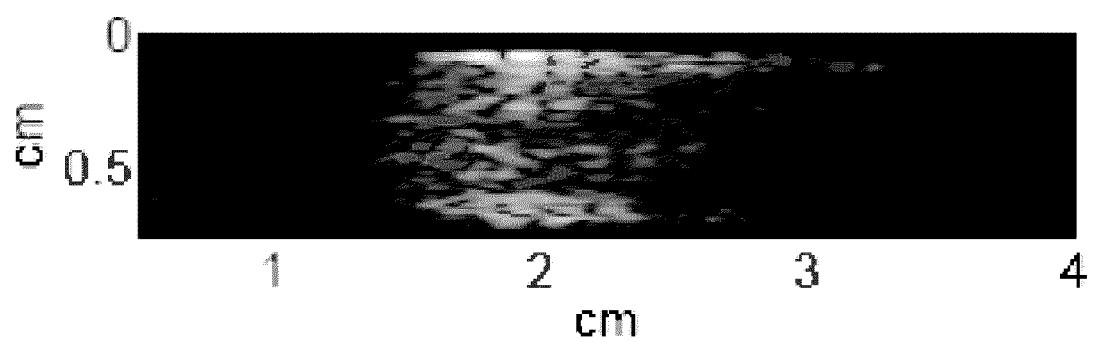
Fig. 18

METHODS AND SYSTEMS FOR SPATIALLY MODULATED ULTRASOUND RADIATION FORCE IMAGING

CROSS-REFERENCE TO RELATED APPLICATION

This application claims the benefit of priority to U.S. provisional patent application Ser. No. 61/285,339 filed Dec. 10, 2009, now pending, the disclosure of which is incorporated herein by reference.

This invention was made with government support under 1R21 EB008724 and 1R01 EB008368 awarded by the National Institutes of Health. The government has certain rights in the invention.

FIELD OF THE INVENTION

The invention relates to the field of ultrasound, and more particularly to ultrasonic imaging.

BACKGROUND OF THE INVENTION

Methods for quantitative imaging of tissue shear modulus using acoustic radiation force induced shear waves have been proposed. Tissue shear modulus is thought to have significant diagnostic utility, and provides an image contrast mechanism distinct from that of conventional imaging modalities, e.g. B-mode ultrasound, X-ray CT. The ability to reliably quantify tissue modulus may reduce the need for tissue biopsy, and can allow longitudinal tracking of tissue response to therapy. (Edwin L. Carstensen, Kevin J. Parker, and Robert M. Lerner, "Elastography in the management of liver disease," Ultrasound in Medicine and Biology, 34(10):1535-1546, 2008.) The use of acoustic radiation force to generate shear waves in tissue for the purpose of tissue characterization was first proposed by Sarvazyan. (Armen P. Sarvazyan, Oleg V. Rudenko, Scott D. Swanson, J. Brian Fowlkes, and Stanislav Y. Emelianov, "Shear wave elasticity imaging: a new ultrasonic technology of medical diagnostics," Ultrasound in Medicine and Biology, 24(9):1419-1435, November 1998.)

Supersonic Shearwave Imaging (SSI), described by Bercoff, Tanter, and Fink, estimates tissue viscoelastic properties by tracking the progress of radiation force induced shear waves with an ultrafast scanner. (Jeremy Berco, Mickael Tanter, and Mathias Fink, "Supersonic shear imaging: A new technique for soft tissue elasticity mapping," IEEE Transactions on Ultrasonics, Ferroelectronics and Frequency Control, 51(4):396-409, April 2004.) Multiple ultrasound tone bursts focused at a sequence of depths and transmitted in rapid succession are used to create a pair of large amplitude shear waves. The propagating shear waves are distorted by variations in shear modulus. Inversion algorithms applied to the tracked motion data are used to recover the shear modulus.

Palmeri et al. propose the Time-To-Peak (TTP) algorithm for shear modulus estimation. (M. L. Palmeri, M. H. Wang, J. J. Dahl, K. D. Frinkley, and K. R. Nightingale, "Quantifying hepatic shear modulus in vivo using acoustic radiation force," Ultrasound in Medicine and Biology, 34(4):546-558, 2008). In this method a shear wave is generated by the acoustic radiation force of a short (10's of μs) focused ultrasound toneburst. Tissue motion lateral to the push beam is then tracked at multiple locations. The time to peak displacement at each location is taken as the "arrival time" of the shear wave. Knowledge of the arrival times and distance between the tracking locations allows the shear wave speed $c_s$ to be estimated. The shear modulus G is then determined through the relationship $G=\rho c_s^2$, where $\rho$ is the tissue density. A linear regression analysis of the measured arrival times is used to make the method more robust to noise.

The method of Shear Dispersion Ultrasound Vibrometery (SDUV) uses a time-varying radiation force to generate a harmonic shear wave. (S. Chen, M. Fatemi, and J. F. Greenleaf, "Shear property characterization of viscoelastic media using vibrations induced by ultrasound radiation force," In Proceedings of the IEEE International Ultrasonics Symposium, volume 2, pages 1871-1875, 2002.) Ultrasonic tracking then measures tissue motion at known distances from the vibration source. The phase shift as a function of distance from the point of excitation is estimated from the motion data to determine the shear wavelength $\lambda$. Coupled with the known vibration frequency f, the shear modulus can estimated as $G=\rho(\lambda f)^2$.

In the TTP and SDUV methods, the propagation path length for the shear waves is assumed to be equal to the distance between the axes of the tracking beams used to measure the passage of the shear wave. With this assumption, estimation of shear wave speed would seem to be a simple matter of determining the time required by the shear wave to propagate past two observation points. However, a significant variance in the shear wave speed estimate is observed with this method, even within a homogeneous phantom. (M. L. Palmeri, M. H. Wang, J. J. Dahl, K. D. Frinkley, and K. R. Nightingale, "Quantifying hepatic shear modulus in vivo using acoustic radiation force," Ultrasound in Medicine and Biology, 34(4):546-558, 2008; Stephen McAleavey, Erin Collins, Johanna Kelly, Etana Elegbe, and Manoj Menon, "Validation of smurf estimation of shear modulus in hydrogels," Ultrasonic Imaging, 31:111-130, 2009.) The variation is consistent at a given observation point and not due to inadequate SNR. Therefore it cannot be reduced by temporal averaging, and spatial averaging of measurements is required to reduce the estimate variance. This spatial averaging, of course, reduces spatial resolution.

Our previous results suggest that the measurement noise is due to a speckle-induced variation in the effective distance between the track beams. (Stephen McAleavey, Erin Collins, Johanna Kelly, Etana Elegbe, and Manoj Menon, "Validation of smurf estimation of shear modulus in hydrogels," Ultrasonic Imaging, 31:111-130, 2009.) Interference of the echo signal from discrete scattering sources within the tissue gives rise to areas of strong and weak reflection. The tracked echo along a given line will reflect the motion of the scatterers that most constructively interfere. These scatterers are not necessarily located on the beam axis, but are potentially displaced from it. The distance between the tracked points is not, then, simply the distance between the axes of ultrasound tracking beams, but rather a function of the two-way beam pattern and scatterer distribution at a given depth. A similar effect was noted by Ophir et al. in pulse-echo estimates of ultrasonic sound speed estimation. (J. Ophir, W. Johnson, Y. Yazdi, D. Shattuck, and D. Mehta, "Correlation artifacts in speed of sound estimation in scattering media," Ultrasound in Medicine and Biology, 15(4):341-353, 1983.) Tracking beam spacings are on the order of 1-4 mm, while beamwidths can be on the order of 0.2-0.5 mm. Thus, this speckle-induced uncertainty in the path length can be a substantial fraction of the path length.

Typical ultrasound backscatter medical imaging systems (e.g., B-scan) use an aperture which is large compared to the ultrasound wavelength to generate a focused beam pattern on transmit and receive. Geometric focusing, either mechanical, electronic, or a combination of the two, is used to determine the phase of the aperture motion on transmit, and to adjust the echo phase on receive. In the linear theory, the frequency, size and apodization of the aperture determine the beam pattern. Deviations in assumed sound speed ($c_i$=1540 m/s typically) of the media between the transducer and target can degrade the ideal beam pattern.

Often, as in medical imaging, the target to be imaged can support shear waves in addition to the longitudinal waves used for ultrasound imaging. Because of the near-incompressibility of tissue (Poisson's ratio nearly equal to 0.5), the shear wave speed is much lower than the longitudinal wave speed, and shear wave motion in the target can be tracked ultrasonically, as in many methods of elasticity imaging. The goal in elasticity imaging is to reconstruct the shear modulus of the object. The shearing of scatterers tends to decorrelate echo signals and ordinarily acts as a noise source (McAleavey et al., "Validation of SMURF estimation of shear modulus in hydrogels").

BRIEF SUMMARY OF THE INVENTION

Spatially Modulated Ultrasound Radiation Force (SMURF) is applied to imaging of shear modulus in tissue-mimicking phantoms and tissues. Uniform phantoms served to verify the calibration of our system through comparison with unconfined compression (Young's Modulus) testing. Phantoms containing spherical and conical inclusions were imaged to demonstrate the ability to resolve structures of varying modulus.

SMURF uses impulsive acoustic radiation force to generate a shear wave of known spatial frequency in a medium of unknown shear modulus. The velocity of the induced shear wave, and hence the shear modulus of the medium, is determined from the period of the induced shear wave. Here we present the first experimentally obtained images of shear modulus using the SMURF method. Images of spherical, conical, and step edge phantoms are presented. Agreement within 8% is found between SMURF and unconfined compression measurements of uniform phantoms. Image resolution on the order of the push beam spacing is observed. A key advantage of this method is that tracking is performed along a single a-line, avoiding correlated noise bias errors encountered in multiple-track location methods. The source of this noise is described below. Modulus estimates are obtained without extensive spatial averaging, allowing high resolution to be obtained.

In contrast, the SMURF method performs tracking along a single A-line while pushing at two or more locations. The shear wave speed is estimated from the difference in arrival times of the pulses, and the path length difference is assumed to be equal to the offset in the push beam locations. The critical difference between this method and those described above is that the tracking takes place at a single location. The location of a speckle at a particular depth may bias the arrival time estimate of a shear wave from one pushing location. However, the same bias will be applied to all shear waves propagating in the same direction. Estimation of the arrival time difference will subtract away any constant bias in the measurement. A speckle-induced uncertainty in the location of the push beams does not exist, because the radiation force is overwhelmingly determined by the attenuation of the medium rather than its scattering. (K. J. Parker, "Ultrasonic attenuation and absorption in liver tissue," Ultrasound in Medicine and Biology, 9(4):363-369, 1983.) (A possible exception is at strongly reflecting boundaries, as between organs. In the bulk of tissues, scattering is assumed to be weak and to make a negligible contribution to the radiation force.) The scattering contribution to the radiation force is small, and the location of the push beam is well represented by the push beam axes.

A challenge for the SMURF method is the viscoelastic nature of tissues. Our previous development of the SMURF method assumed a linear elastic model that neglected shear wave dispersion. We have found that dispersion effects complicate the application of SMURF in strongly viscoelastic media, e.g. liver tissue. We have developed and present here a modified sequence, denoted as SMURF-mod. Briefly, the SMURF-mod method introduces a time delay between each push beam spatial peak. This delay allows individual shear wave peaks generated by the push beam sequence to be more easily detected, while retaining the advantages of a single tracking location.

An objective of this disclosure is to demonstrate shear modulus imaging with SMURF. The standard SMURF method is compared with the modified sequence in elastic phantoms. We demonstrate that the two methods provide equivalent results in elastic media. Images of modulus are found to be similar with both methods in elastic spherical and conical phantoms. Modulus estimates in homogeneous phantoms are also shown to agree within the estimate standard deviations. SMURF-mod is found to be superior in liver tissue, while SMURF with similar push beam spacing does not yield a useful modulus estimate. As described in the Methods section, SMURF-mod is slightly more time consuming, as it requires more tracking echoes to generate an estimate.

The application of Spatially Modulated Ultrasound Radiation Force (SMURF) to shear modulus imaging is demonstrated in tissue mimicking phantoms and porcine liver. Scanning and data acquisition was performed with a Siemens Antares ultrasound scanner and VF7-3 linear array operating at 4.21 MHz. Modulus estimates in uniform phantoms of Zerdine with shear moduli of 5.1 and 12.4 kPa exhibited standard deviations within 6% of the mean value. Zerdine spheres 1 cm in diameter (nominally 2.7, 4.7, and 15 kPa) in a 8 kPa (nominal) background are clearly resolved. Cross sectional images of a soft conical inclusion in a gelatin-based phantom indicate a spatial resolution of approximately 2.5 mm. Images of the shear modulus of an ex-vivo sample of porcine liver tissue show an average value of 3 kPa. A stiff lesion induced with 0.5 mL of 10% glutaraldehyde is clearly visible as a region of shear modulus in excess of 10 kPa. A modulus gradient associated with the diffusion of the glutaraldehyde is visible. Two pulse sequences were examined, differing only in the timing of the beams used to generate the shear waves. Details of the beam sequences and subsequent signal processing are presented.

A method to reconstruct a image of the ultrasonic echogenicity of the target under the assumption of uniform shear modulus is presented. We show that in this method the lateral resolution is independent of the aperture size and instead determined by the shear wave velocity in the target and by the range of shear wave frequencies that can be applied to the target.

Conventional ultrasound imaging uses mechanically focused transducers and/or delay-and-sum beamforming to focus transmit and receive beams and provide lateral resolution. Lateral resolution is determined by aperture size and wavelength. A sound speed of 1540 m/s is typically assumed; sound speed variations may degrade the focus. We present a novel method in which lateral resolution of the target is obtained by using traveling shear waves to encode the lateral position of targets in the phase of the received echo. This method separates the lateral resolution of the imaging system from the properties of the ultrasound aperture. We demonstrate image formation with an unfocused transducer in phantoms of uniform shear modulus.

DESCRIPTION OF THE DRAWINGS

For a fuller understanding of the nature and objects of the invention, reference should be made to the following detailed description taken in conjunction with the accompanying drawings, in which:

FIG. 2A is SMURF with no pre-processing, G=5.5±0.7 kPa; FIG. 2B is SMURF with autocorrelation-fit processing, G=5.59±0.19 kPa; and FIG. 2C is SMURF-mod, G=5.73±0.18 kPa.

(FIG. 4B) SMURF image, unfiltered; and (FIG. 4C) SMURF image with 1 mm×1 mm spatial median filter.

FIGS. 7A-7I are shear modulus images of 1 cm diameter inclusions in CIRS Model 049 phantom. A push beam spacing of 2.48 mm was used for all images. Top row: Type I lesion, imaged with (7A) B-mode, (7B) SMURF, and (7C) SMURF-mod sequence. Middle row: Type II lesion, imaged with (7D) B-mode, (7E) SMURF, and (7F) SMURF-mod sequence. Bottom row: Type III lesion, imaged with (7G) B-mode, (7H) SMURF, and (7I) SMURF-mod sequence. The modulus images have been subjected to a 1 mm×1 mm spatial median filter.

FIGS. 10A-10H are cross-sectional images of the conical section within the gelatin phantom. A 1 mm×1 mm spatial median filter has been applied to the SMURF images.

FIGS. 17A-17B are images of nylon monofilament wires in a gelatin block as imaged by the shear wave method. The images are displayed on a 20 dB (FIG. 17A) or 40 dB (FIG. 17B) dynamic range grayscale.

FIG. 18 is an image of the hyperechoic cylinder in the gelatin block phantom reconstructed from experimental shear wave modulated data. The displayed dynamic range is 30 dB.

DETAILED DESCRIPTION OF THE INVENTION

Figure 19:
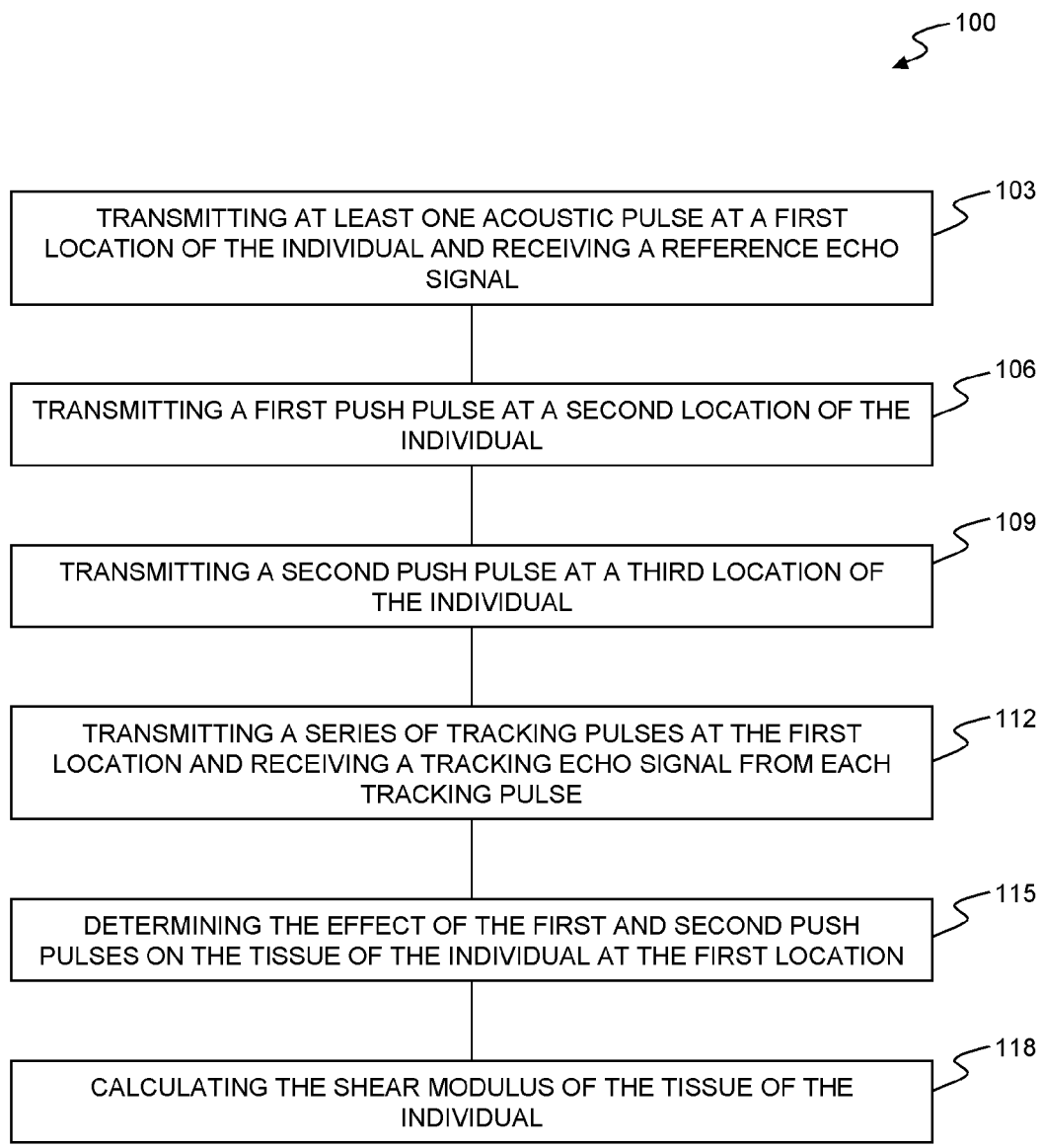
FIG. 19 is a flowchart depicting a method according to an embodiment of the present invention.

In a method 100 according to an embodiment of the invention (FIG. 19) the shear modulus of a tissue of an individual may be determined. An acoustic pulse is transmitted 103 at a first location of the individual, and an echo signal is received to establish a reference echo signal. This transmit/receive ensemble may be, for example but not limited to, a standard B-mode ultrasound pulse and the corresponding echoes created by that pulse in the tissue. Two or more acoustic pulses may be used to determine the reference. A first push pulse is transmitted 106 at a second location of the individual. The first push pulse may cause a shear wave to be transmitted through the tissue. A second push pulse is transmitted 109 at a third location of the individual. The second push pulse may cause a shear wave to be transmitted through the tissue. The first push pulse, the second push pulse, or both push pulses may be formed by a 200 cycle toneburst having a center frequency of 4.21 MHz. The second location (where the first push pulse is transmitted) and the third location (where the second push pulse is transmitted) may be located on a same side of the first location (see, e.g., FIG. 1A).

A series of tracking pulses are transmitted 112 at the first location and a tracking echo signal is received from each tracking pulse. The tracking pulses may be B-mode ultrasound pulses. As further described below, the effect of the first and second push pulses on the tissue is determined 115 through analysis of the tracking echo signals. For example, the displacement of tissue at the first location and caused by the push pulses (for example, the shear wave created by the push pulses) can be determined through the time series tracking echo signals. The shear modulus of the tissue is calculated 118 based on the effect of the push pulses on the tissue. For example, the timing of the displacement of the tissue (compared to the reference echo signal and/or compared over time) at the first location may indicate the speed of the shear wave, which may vary based on the shear modulus. A detailed discussion of this is contained below.

Figure 20:
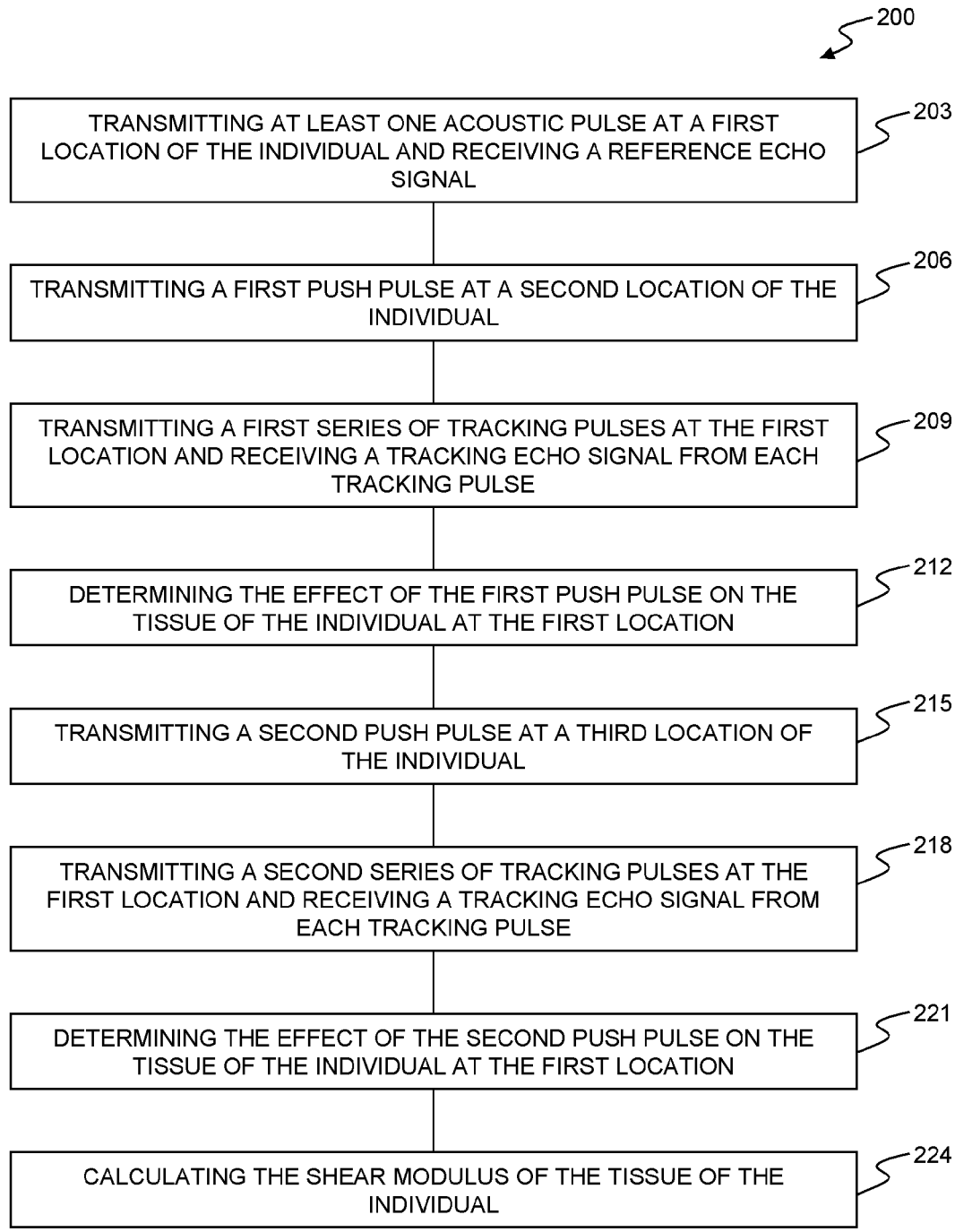
FIG. 20 is a flowchart depicting a method according to another embodiment of the present invention.

In an alternative embodiment (depicted in FIG. 20), a method 200 for determining the shear modulus of the tissue of an individual comprises the step of transmitting 203 an acoustic pulse at a first location of the individual, and receiving an echo signal is received to establish a reference echo signal. A first push pulse is transmitted 206 at a second location of the individual. The first push pulse may cause a shear wave to be transmitted through the tissue. A first series of tracking pulses are transmitted 209 at the first location and a first set of tracking echo signals is received. Each tracking echo signal of the first set of tracking echo signals corresponds to a tracking pulse of the first series of tracking pulses. The first series of tracking pulses may comprise 30 tracking pulses. The effect of the first push pulse on the tissue is determined 212 through analysis of the first set of tracking echo signals.

A second push pulse is transmitted 215 at a third location of the individual. The second push pulse may cause a shear wave to be transmitted through the tissue. A second series of tracking pulses are transmitted 218 at the first location and a second set of tracking echo signals is received. Each tracking echo signal of the second set of tracking echo signals corresponds to a tracking pulse of the second series of tracking pulses. The second series of tracking pulses may comprise 40 tracking pulses. The effect of the second push pulse on the tissue is determined 221 through analysis of the second set of tracking echo signals.

The shear modulus of the tissue is calculated 224 based on the effect of the push pulses on the tissue.

Figure 21:
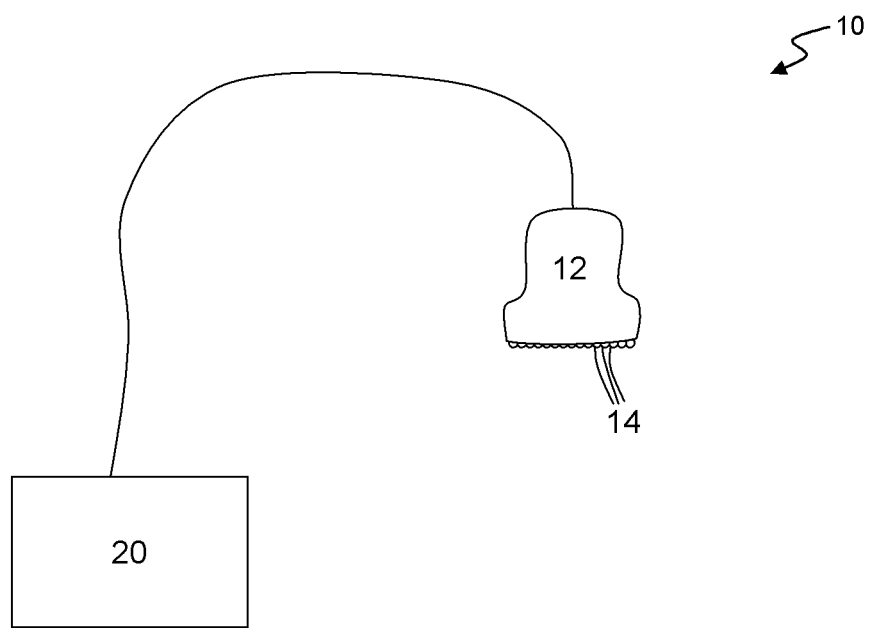
FIG. 21 is a schematic of a system according to an embodiment of the present invention.

The present invention may also be embodied as a system 10 for producing an image of a region of tissue of an individual (see, e.g., FIG. 21). The system 10 comprises an ultrasonic transducer 12 for transmitting acoustic pulses. The ultrasonic transducer 12 is further used to receive echo signals. The ultrasonic transducer 12 may have an addressable array of ultrasonic elements 14. Each element 14 may be capable of transmitting acoustic pulses and receiving echo signals.

The system 10 further comprises a controller 20 is communication with the ultrasonic transducer 12. The controller 20 is programmed to cause a first set of elements 14 of the ultrasonic transducer 12 to transmit and receive an ensemble of acoustic pulses and corresponding echo signals at a tissue at a first location of the region of tissue. The ensemble may be configured as in the methods 100, 200 described above. The controller 20 is further programmed to calculate a shear modulus of the tissue at the first location of the region. A second set of elements 14 may transmit and receive the ensemble at the tissue at a second location of the region of tissue. The controller 20 is further programmed to calculate the shear modulus of the tissue at the second location. The controller 20 is programmed to repeat the transmission and reception of the ensemble using different sets of elements 14 of the transducer 12 until the shear modulus of the tissue of the entire desired region of tissue has been determined. The controller 20 is programmed to generate an image by compiling the shear modulus of each tissue of the region of tissue. For example, an image may be generated wherein the intensity of a pixel of the image corresponds to the shear modulus of the tissue represented by said pixel.

The present invention is further described below with reference to experimental application. The below examples are intended to be non-limiting.

Methods

A. Beam Sequences

Figure 1A:
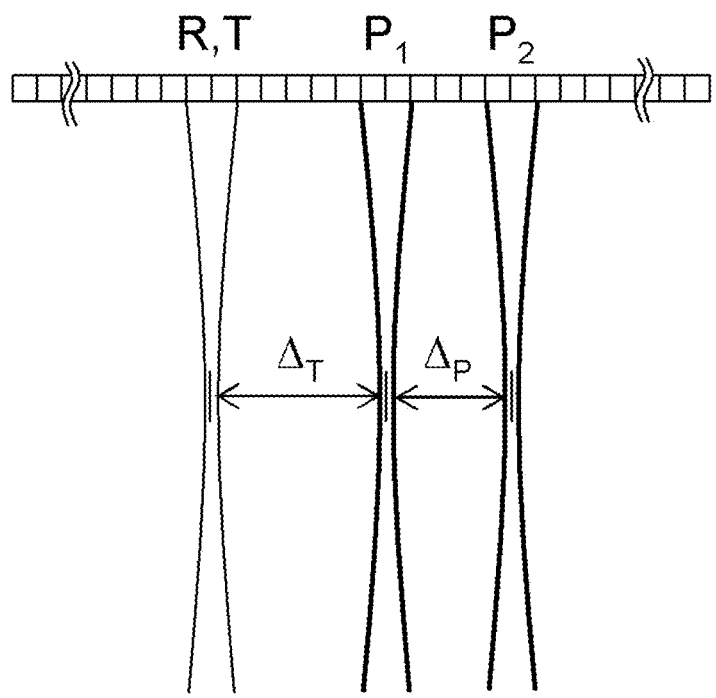
FIG. 1A is a schematic illustration of pulse sequences used in generating shear modulus images showing the relative locations of reference/tracking beams (R,T) in relation to the two push beams ($P_1$, $P_2$). The push beams are separated by lateral distance $\Delta_P$ while the track beam is displaced by $\Delta_T$ from the left push beam. The relative push and track locations are the same for both sequence types and all ensembles; the ensembles are walked across the aperture to build up an image.

All imaging was performed with a Siemens Antares scanner (Siemens Medical Solutions, USA, Ultrasound Group) and VF7-3 linear array transducer. Echo data were collected at 40 MHz and digitized with 16-bit resolution. Each SMURF pulse ensemble contained two types of pulses—"tracking" and "pushing" pulses. Tracking pulses are standard B-mod-estyle pulses used to follow the motion of tissue in response to applied radiation forces, focused at 1.5, 2, 2.5 or 3 cm here. Dynamic focusing and apodization was applied to the received echoes. Pushing pulses for generating displacements were 200 cycle (47.5 µs) tonebursts of 4.21 MHz center frequency, F/3.5 aperture. Push and track beam focal depth were matched in all cases. Two ensemble types were implemented. The geometric relationship between beams in the sequences is illustrated in FIG. 1A.

In the first type (SMURF), a tracking pulse is transmitted at one scan line to generate a reference echo. Two pushing pulses are then launched parallel to the track, separated laterally from each other by $\Delta_P$, and from the track beam by $\Delta_T$. Tracking echoes are then collected along the same scan line as the reference echo. In these experiments the pulse period (time between start of each pulse) was 134 µs, $\Delta_P$ was 2.48 mm, and $\Delta_T$ was 1.8 mm. The value of $\Delta_P$ was chosen such that the first lateral null of the one push beam aligns with that of the other push beam, maximizing the intensity variation in the region of interest.

The second ensemble type (SMURF-mod) differs from the first in that tracking pulses are inserted between the first and second push pulses. Following the first push pulse, 30 tracking pulses are transmitted and echoes collected to measure the tissue motion. The second push pulses is then transmitted, translated laterally by $\Delta_P$ relative to the first push pulse beam axis and $\Delta_P+\Delta_T$ relative to the tracking beam axis. Forty tracking pulses are then transmitted and echoes collected at the tracking beam location.

Images were derived from 60 (SMURF) or 40 (SMURF-mod) ensembles, with a lateral translation of 0.53 mm between ensembles, for a lateral field of view of 3.2 cm (SMURF) or 2.1 cm (SMURF-mod). In all cases RF echo data was collected over a 0-4 cm axial window.

B. Signal Processing

Target displacement was measured using normalized cross correlation of windowed segments of the RF echo signals, as described in "Validation of SMURF estimation of shear modulus in hydrogels" (supra). 1.5 μs (1.2 mm) long correlation windows were used. Cross correlation of upsampled echo data (320 MHz sampling) followed by parabolic interpolation of the correlation function was used to determine the location of the peak with sub-sample precision. The resulting discrete time measurements of displacement d[z, m], a function both of target range z and echo index m were converted to a velocity estimate v[z, m] by the finite difference approximation v[z, m]=(d[z, m+1]−d[z, m])·PRF, where PRF is the tracking pulse repetition frequency. For SMURF echo sequences, the tracking process results in a single two dimensional matrix v of velocity estimates vs. depth and time, while for SMURF-mod pulse sequences the velocity data are split into two matrices, $v_1$ and $v_2$, the velocity estimates associated with the first and second pushing pulses.

To estimate modulus from the SMURF data sets, the autocorrelation R of the discrete time velocity estimate $v_z[n]$ was calculated at each depth z, $$R_v[m] = \sum_n v[z, n]v[z, n+m]. \quad (1)$$

The lag corresponding to the period of the vibration signal at depth z was taken to be the lag of the peak of $R_{v,z}[m]$ in the range $m_{min} < m < \infty$, where $m_{min}$ is the lag of the minimum $R_{v,v}$ for a given z. The frequency f of the SMURF-induced shear wave is taken to be the reciprocal of the lag of the identified local maximum of R. The shear modulus G was then calculated as $$G = \rho(\Delta_p f)^2 \frac{1}{(1-fT)^2}, \quad (2)$$

where T is the time between push pulses, and ρ the material density (assumed to be 1.0 g/cm³). The factor of $1/(1-fT)^2$ is a correction term arising from the propagation of the shear wave due to the first pushing pulse before the transmission of the second pulse. This early propagation increases the effective spacing between beams. Identification of the autocorrelation peak was improved by suppression of low-frequency components of the velocity signal, due either to transducer motion or the low-frequency, non-spatially modulated component of the velocity signal (S. A. McAleavey, M. Menon, and J. Orszulak, "Shear-modulus estimation by application of spatially modulated impulsive acoustic radiation force," Ultrasonic Imaging, Vol 29, pp. 87-104, April 2007). This was achieved by subtracting a second order polynomial fit from the autocorrelation signal at each depth.

Cross-correlation of the velocity signals $v_1$ and $v_2$ at each depth z was used to determine the difference in arrival time τ between the first and second push pulses of the SMURF-mod data sets Cross correlation was calculated as $$C_{v1,v2}[m] = \sum_n v_1[z, n]v_2[z, n+m]. \quad (3)$$

The location of the global maximum of $C_{v1,v2}[m]$, denoted τ, was taken as the arrival time difference between the two shear waves. The modulus is thus $$G = \rho(\Delta_p/\tau)^2. \quad (4)$$

For both pulse sequences the shear wave propagation paths are identical except for the difference $\Delta_P$. The estimated modulus thus corresponds to the modulus of the region between the pushing pulses.

C. Phantoms

A homogeneous cylinder (5.1 cm diameter by 2.4 cm height) of Zerdine™ tissue-mimicking material (Computerized Imaging Reference Systems, Inc, Norfolk, Va.) were used for verification of calibration. The shear modulus determined by unconfined compression was 5.1 kPa. A CIRS Model 049 Elastography Phantom was used as a test target for imaging (Computerized Imaging Reference Systems, Inc, Norfolk, Va.). This phantom is ultrasonically tissue mimicking with a sound speed of 1540 m/s and attenuation of 0.5 dB/cm/MHz. The phantom contains spherical inclusions that appear isoechoic with respect to the background in B-mode but differ significantly in shear modulus. Spheres 1 cm in diameter, centered 2.5 cm below the scanning surface, were imaged. Last, a gelatin phantom with conical and cylindrical inclusions was imaged. The inclusions were half the modulus of the background. The conical section has a height of 33 mm and base diameter 12 mm. Cross sectional and longitudinal scans of the conical section were obtained.

Results

Figure 2A:
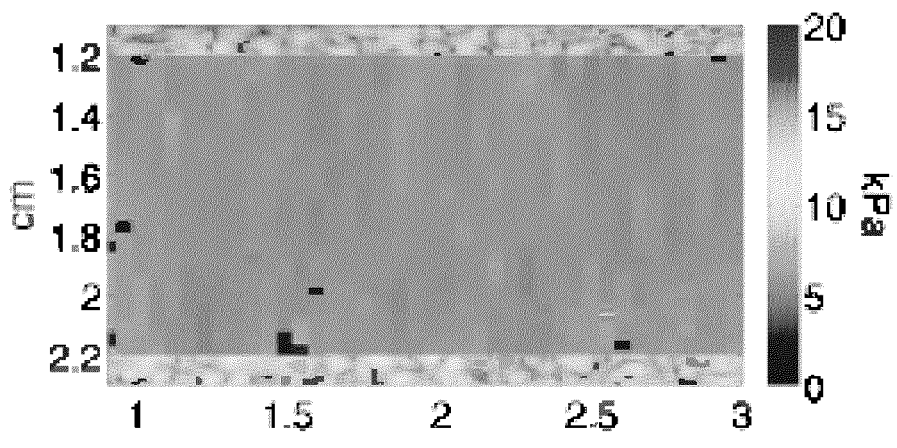
FIGS. 2A-2C are images of uniform Zerdine phantoms. No postprocessing filtering has been applied.
Figure 2B:
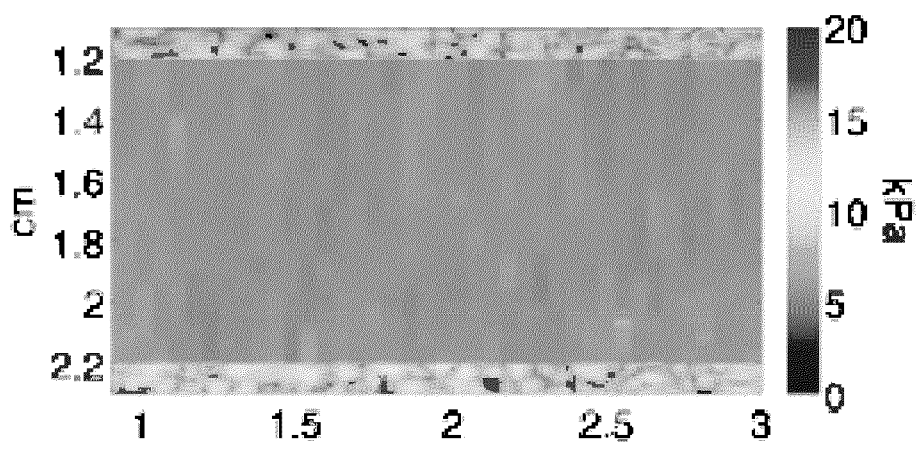
Figure 2C:
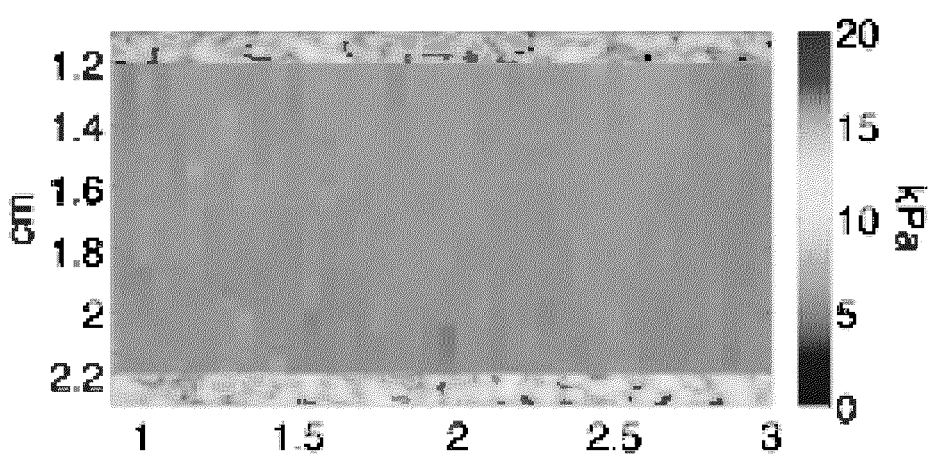
Figure 3A:
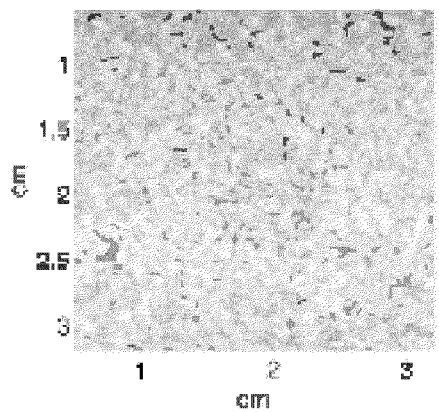
FIGS. 3A-3E are shear modulus images of 1 cm diameter inclusions, CIRS Model 049 phantom. Top row: B-mode Type I (a), Type III (b). Middle row: Matched SMURF with autocorrelation filtering. Bottom row: Matched SMURF-mod images. The modulus images have been subjected to a 1 mm×1 mm spatial median filter.
Figure 3B:
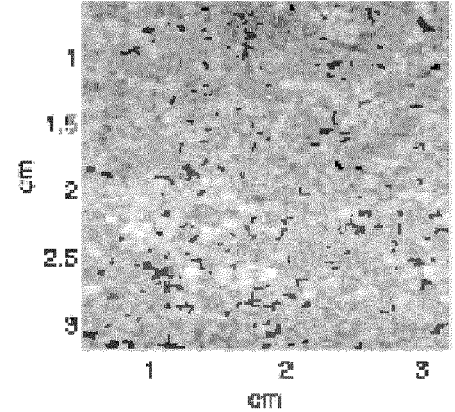
Figure 3C:
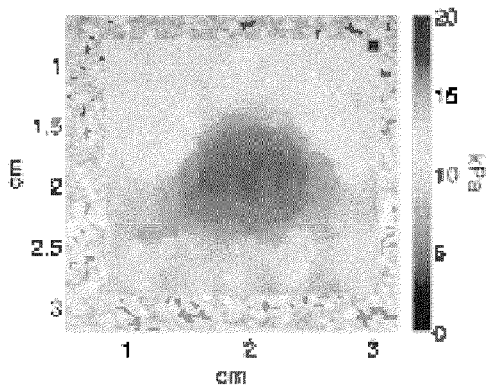
Figure 3D:
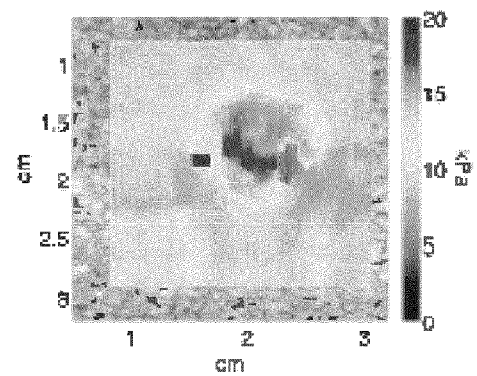
Figure 3D:
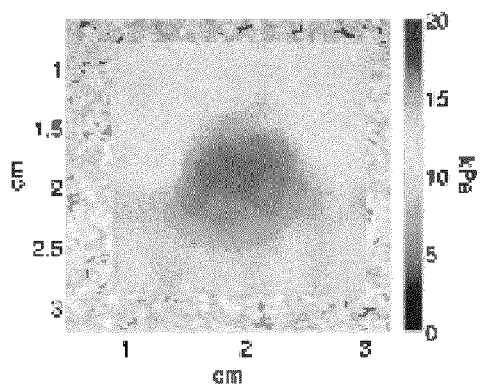
Figure 3E:
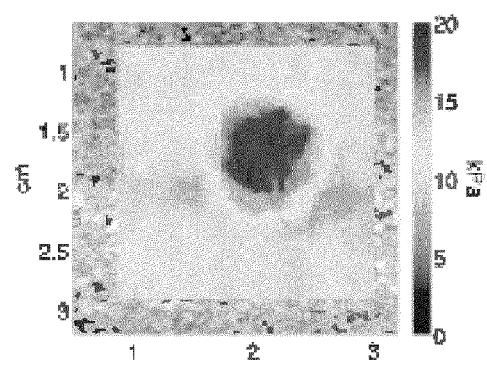

Shear modulus images of the uniform Zerdine cylinder are presented in FIGS. 2A-2C. The mean value estimated by each method phantom mean values agree within the associated standard deviation across each of the beam sequences. Noise in the no-pre-processing SMURF image, visible as spots of erroneously low modulus estimate, is caused by a failure of the algorithm to identify the correct autocorrelation peak. This noise is effectively eliminated by the autocorrelation fit procedure described in the Methods section. The cross-correlation method does not face errors of this sort as the shear wave pulses are well resolved in time.

Matched B-mode, SMURF, and SMURF-mod images of spherical inclusions are shown in FIGS. 3A-3E. Modulus values for the lesions are consistent for both estimators. The artifact in the SMURF image of stiff lesion is a peak-hop, or false peak, error in estimating the peak of the autocorrelation signal. The apparent lateral resolution of the images is on the order of the 2.5 mm push beam spacing.

Figure 4A:
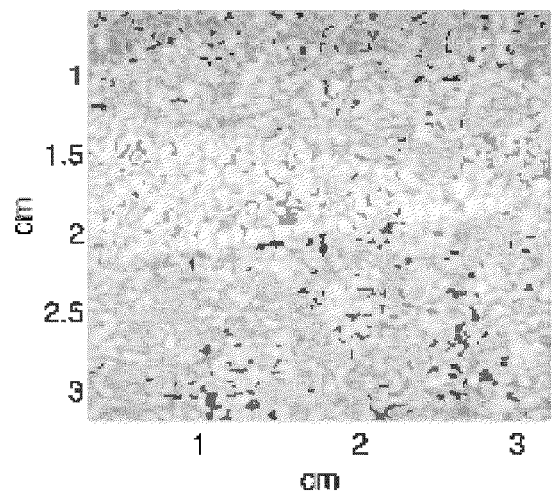
FIGS. 4A-4C are images of a longitudinal cross section of the conical phantom—(FIG. 4A) B-scan.
Figure 4B:
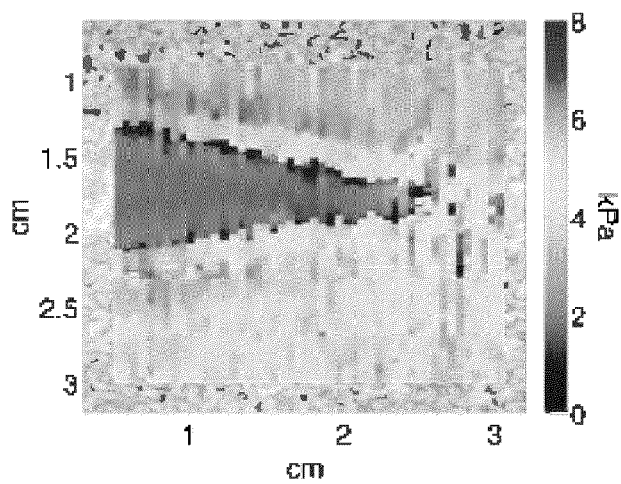
Figure 4C:
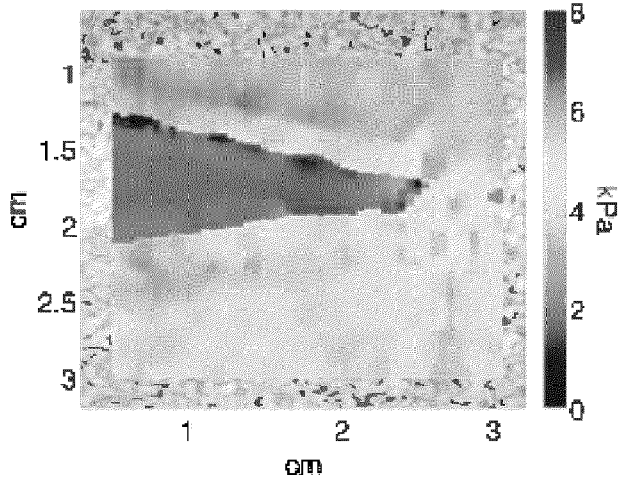
Figures 5A, 5B, 5C, 5D, 5E, 5F:
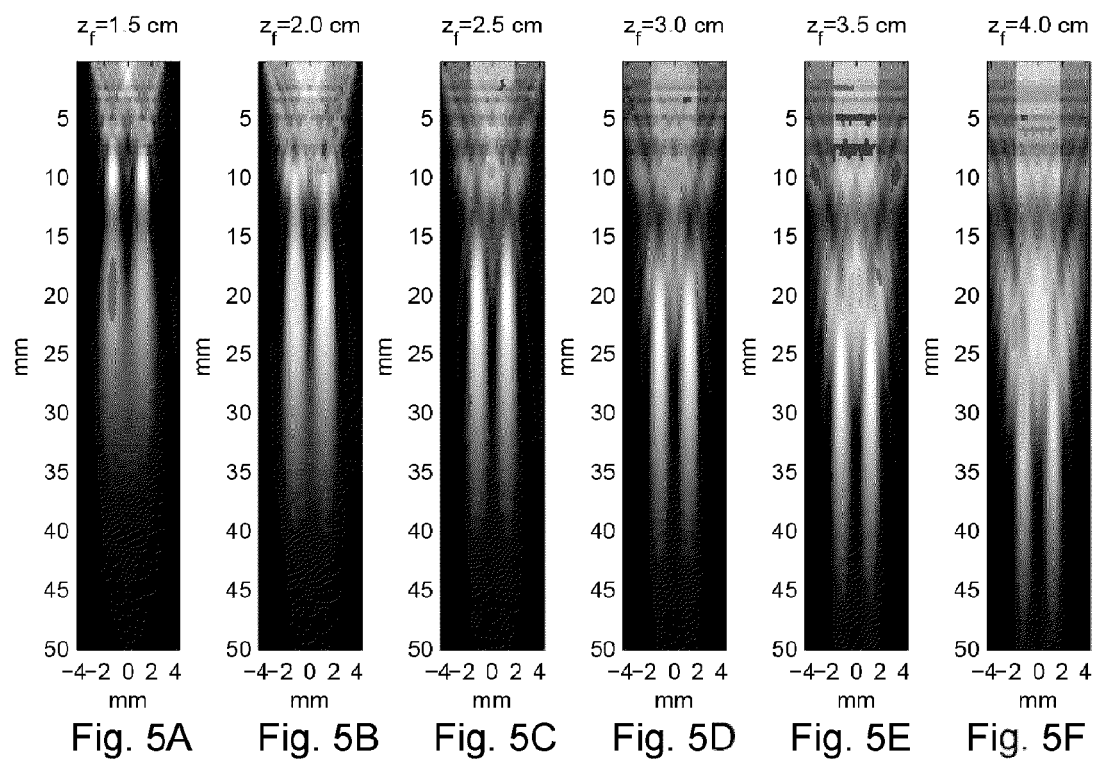
FIGS. 5A-5F are simulated push-beam patterns. The Siemens VF7-3 transducer was modeled using Field 2. The relative intensities of a 4.21 MHz, 100 cycle toneburst in a 0.5 dB/cm/MHz medium was modeled for the focal depths indicated. The images show the total intensity pattern over the two push beam transmissions. The grayscale in each panel is scaled to the peak intensity within the field of view.
Figure 6A:
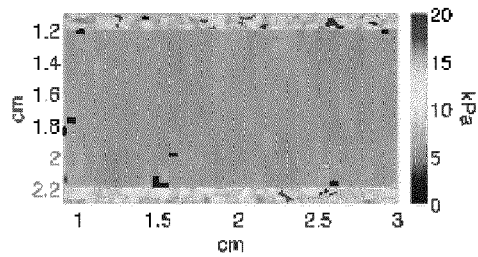
FIGS. 6A-6F are unfiltered modulus images of uniform Zerdine phantoms. Images of the compliant phantom are in the left column; the stiff phantom is on the right. (6A,6B) SMURF without autocorrelation; (6C,6D) SMURF with autocorrelation; and (6E,6F) SMURF-mod.
Figure 6B:
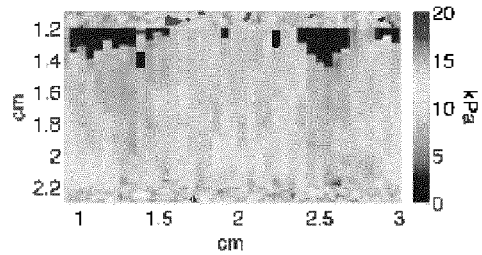
Figure 6C:
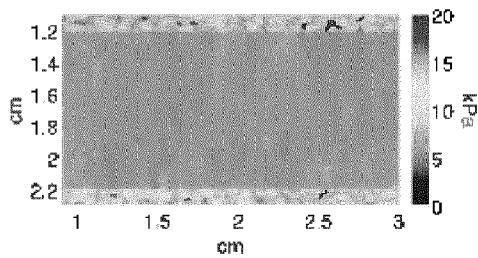
Figure 6D:
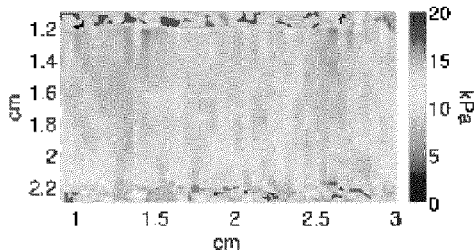
Figure 6E:
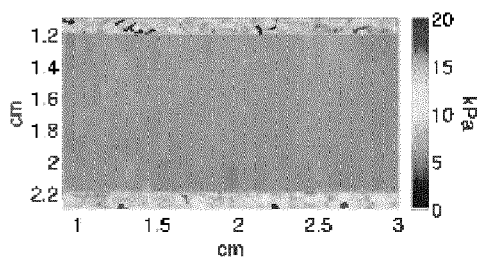
Figure 6F:
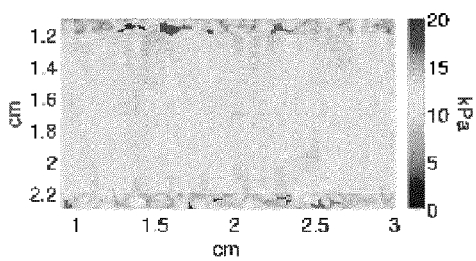
Figure 8A:
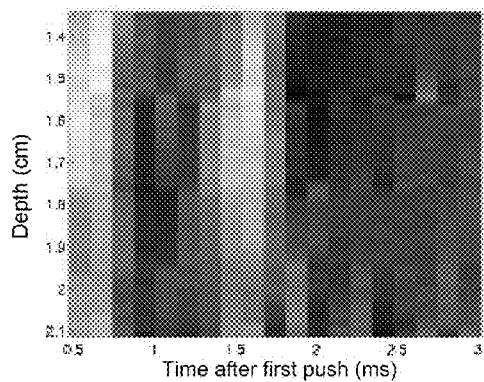
FIGS. 8A-8D are sample velocity vs. time signals and correlation processing. Top Row: v(z,t) signal obtained in the background of the CIRS phantom using (8A) SMURF and (8B) SMURF-mod sequences. Bottom Row: (8C) The autocorrelation of v(z,t) for z=2 cm is plotted with (dot-dash), and without (solid) autocorrelation filtering. In (8D) the cross-correlation signal is plotted for the SMURF-mod sequence. The lags of the peaks in (8C) are greater than the lag of the peak in (8D) due to the time between firing of the two push pulses in the SMURF sequence. This time is not included in the SMURF-mod sequence.
Figure 8B:
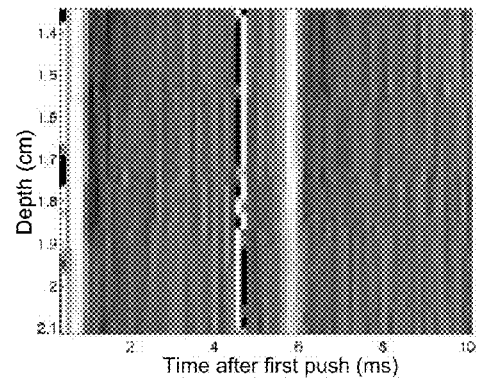
Figure 8C:
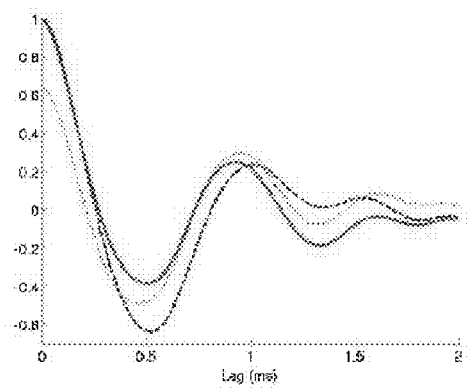
Figure 8D:
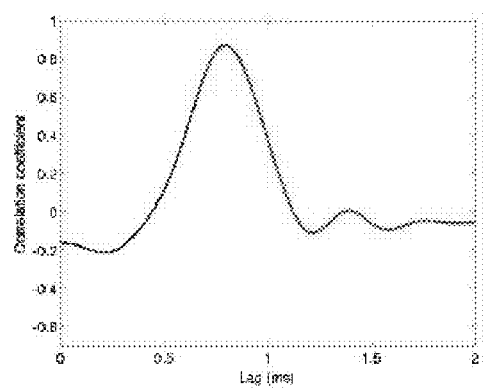
Figure 9A:
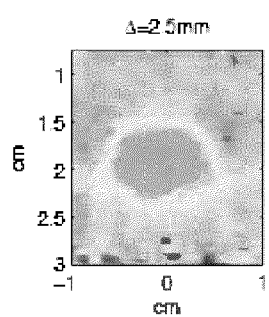
FIGS. 9A-9F are images of Type I phantom obtained with varying push beam spacing using SMURF-mod sequence. Push beam spacings are indicated above each figure. Noise in the modulus estimate increases with decreased push beam spacing.
Figure 9B:
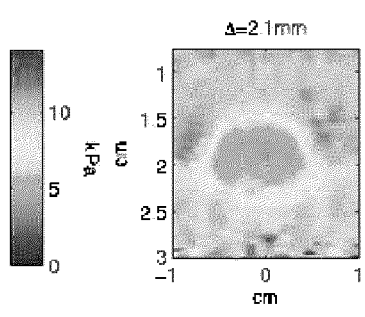
Figure 9C:
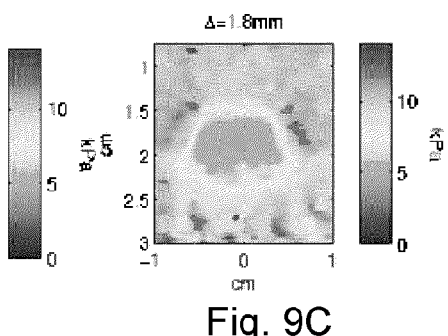
Figure 9D:
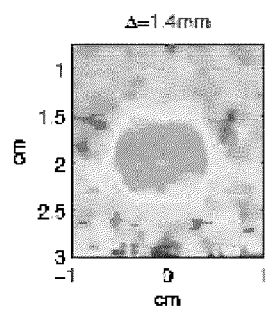
Figure 9E:
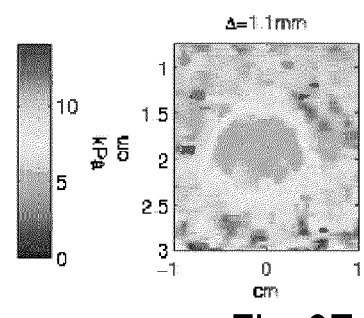
Figure 9F:
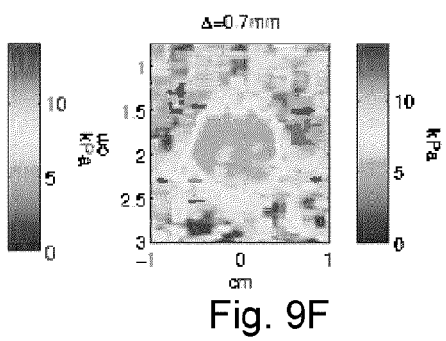
Figure 11A:
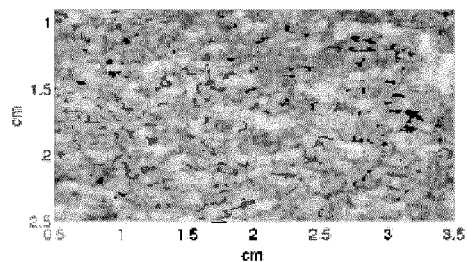
FIGS. 11A-11F are matched B-mode and SMURF-mod images of porcine liver. Bmode (11A) and SMURF-mod (11B) images before injection of 0.5 mL, 10% gluteraldehyde solution. Bscans and SMURF-mod images at 4 minutes post-injection (11C and 11D) and 8 minutes (11E and 11F). Modulus images have been median filtered over a 1×1 mm window.
Figure 11B:
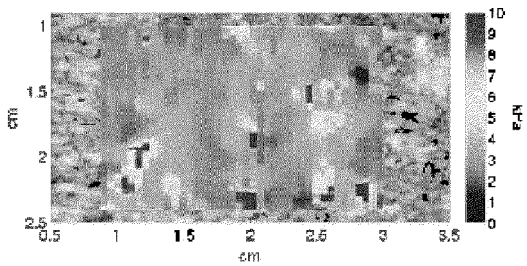
Figure 11C:
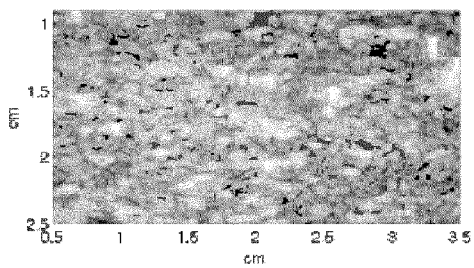
Figure 11D:
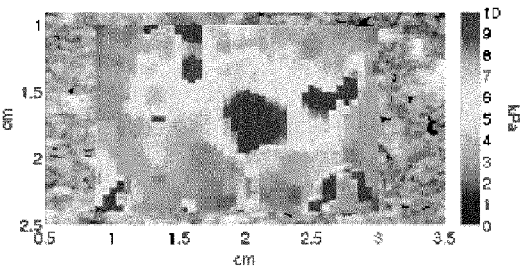
Figure 11E:
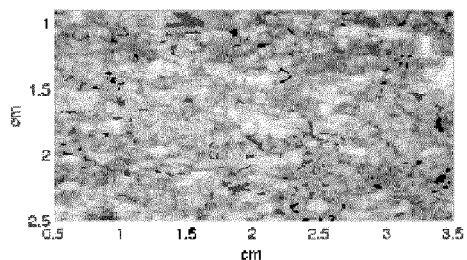
Figure 11F:
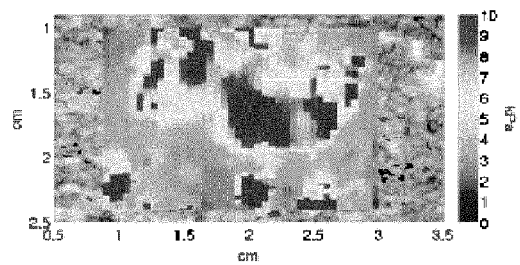

Matched B-mode and modulus images of the cone phantom with the scan plane aligned with the cone axis are shown in FIGS. 4A-4C. The edges between the interior and exterior display a jagged appearance comparable to the speckle size, due to preferential tracking of speckles inside or outside of the cone.

Discussion

Both SMURF and SMURF-mod sequences generate estimates comparable to values obtained by unconfined compression. Detection of the difference in arrival time of peaks in a SMURF ensemble can be complicated by low-frequency motion of the target due to the non-modulated component of the forcing function. The polynomial fit to and subtraction from the autocorrelation simplifies the detection of the secondary autocorrelation peak. The SMURF-mod sequence simplifies the signal processing needed to reconstruct the modulus image. The increased temporal separation makes it easier to time the arrival of the two shear waves. Because of the extra time required to collect the SMURF-mod ensemble, sensitivity to physiological and transducer motion can be expected to increase. The low variance of the modulus estimates suggest that speckle noise is effectively suppressed by this method.

Methods

All imaging was performed with a Siemens Antares scanner (Siemens Medical Solutions, USA, Ultrasound Group). Echo data were collected using the Axius Direct research interface, which allows acquisition of beamformed RF echo data sampled at 40 MHz and digitized with 16-bit resolution. A linear array transducer (Siemens VF7-3) was used for scanning in all cases. This transducer array consists of 192 elements of approximately 0.2 mm pitch and 7.5 mm height. The elevation focus of the array, set by a fixed cylindrical lens, is 3.8 cm.

A. Imaging Sequences

Images of shear modulus are developed from SMURF pulse ensembles. Each ensemble provides an estimate of modulus as a function of range along a ray emanating from the transducer. The grouping of a set of transmitted pulses and corresponding echo signals into an ensemble is conceptually similar to the grouping used to describe a Color Doppler pulse sequence. (C. Kasai, K. Namekawa, A. Koyano, and R. Omoto, "Real-Time Two-Dimensional Blood flow imaging using an autocorrelation technique," IEEE Transactions on Sonics and Ultrasonics, 32:458-463, 1985). Multiple ensembles are transmitted with a uniform lateral translation between each ensemble to sweep out a two dimensional area and allow for image formation. In the exemplary experiments described here with a linear array transducer, a simple translation in x is applied between one ensemble and the next. In the case of a phased array probe, beam steering would be used to sweep ensembles over the region of interest.

Each ensemble consists of two types of pulses—"tracking" and "pushing" pulses. Tracking pulses are standard B-mode-style pulses used to follow the motion of tissue in response to applied radiation forces. These pulses were generated with a single cycle, 4.21 MHz sinewave excitation. Transmit focal depths of 1.5, 2, 2.5 and 3 cm were used, and in all cases apodized to an F-number of 1.8. Dynamic focusing and apodization was applied to the received echoes. Pushing pulses for generating displacements were 200 cycle (47.5 µs) tonebursts of 4.21 MHz center frequency. The focal depth of the push beam was matched to that of the tracking beam, and a uniform F/3.5 apodization was used. Field II simulations of the push beam pattern are illustrated in FIGS. 5A-5F.

Figure 1B:
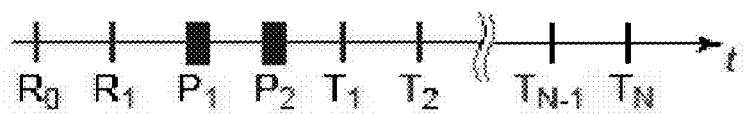
FIG. 1B depicts the timing of the sequential SMURF sequence. Two B-mode style pulses ($R_0$, $R_1$) establish the reference echo to which later tracking pulses ($T_1$-$T_N$) are compared to determine displacement. Pushing pulses $P_1$ and $P_2$ are fired in rapid succession to generate the spatially varying radiation force.
Figure 1C:
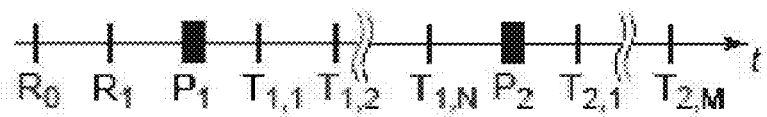
FIG. 1C depicts the timing of the modified SMURF sequence. Following transmission of the reference pulses, a single push beam at $P_1$ is transmitted and tracked with B-mode pulses $T_{1,1}$-$T_{1,N}$. The second pushing pulse is launched at location $P_2$ and tracked with pulses $T_{2,1}$-$T_{2,M}$. All tracking occurs along the same a-line for a given ensemble.

Two ensemble types were evaluated. The pulse sequence for each ensemble type is illustrated schematically in FIGS. 1A-1C. In the first type (SMURF), a tracking pulse is transmitted at one scan line location. The echo, dynamically focused and apodized, is collected to generate a reference A-line. Two pushing pulses are then transmitted in rapid succession. The focus of each push beam is at the same depth z as the tracking beam but translated laterally by $\Delta_P$. The distance between the beam axis of the tracking line and the axis of the first push beam, $\Delta_T$, is independent of the spacing between push beams. A series of tracking pulses is transmitted and echoes collected along the same scan line as the reference echo. Cross correlation processing of the resulting echo signals, as described below, allows the tissue motion in response to the two pushing pulses to be measured. Unless otherwise noted, in the experiments described here the pulse period (time between start of each pulse) was 134 µs, $\Delta_P$ was 2.48 mm, and $\Delta_T$ was 1.8 mm. The value of $\Delta_P$ was chosen such that the first lateral null of the one push beam aligns with that of the other push beam, maximizing the intensity variation in the region of interest. For other values of $\Delta_P$ the push beam F-number should be adjusted to maintain the alignment of the push beam nulls. Since the depth of field is proportional to the F-number squared, there is a trade-off between push beam spacing (i.e. lateral resolution) and depth of field. The value of $\Delta_T$ was selected so that the propagation delay of the shear wave from the first push location to the tracking location was greater than the time required to transmit the second push beam and two tracking beams. This ensured that the entire shear wave would be observed.

The second ensemble type (SMURF-mod) differs from the first in that tracking pulses are inserted between the first and second push pulses. Following the first push pulse, 30 tracking pulses are transmitted and echoes collected to measure the tissue motion. The second push pulses is then transmitted, translated laterally by $\Delta_P$ relative to the first push pulse beam axis and $\Delta_P+\Delta_T$ relative to the tracking beam axis. Forty tracking pulses are then transmitted and echoes collected at the tracking beam location. The extra 10 tracking pulses are added to allow for the extra transit time needed for the shear wave from the second push pulse to reach the tracking beam axis, compared to the shear wave from the first tracking pulse. In both ensemble types all tracking is performed along a single A-line.

SMURF imaging sequences used in this study were made up of 60 ensembles, with a lateral translation of 0.53 mm between ensembles, yielding a lateral field of view of 3.2 cm. SMURF-mod imaging sequences contained 40 ensembles with the same 0.53 mm translation between ensembles, resulting in a 2.1 cm field of view. RF echo data was collected over a 0-4 cm axial window.

B. Signal Processing

All signal processing subsequent to echo collection was implemented in MATLAB (The Mathworks, Natick, Mass.). Tissue displacement relative to the position prior to radiation force excitation was measured using normalized cross correlation of windowed segments of the RF echo signals, as described in McAleavey et al., "Validation of SMURF estimation of shear modulus in hydrogels." The window segments were 1.5 µs long, corresponding to a range window of 1.2 mm. Low-pass interpolation was used to increase the RF sample frequency to 320 MHz. Following calculation of the normalized cross correlation of each echo window with the reference echo, parabolic interpolation of the correlation function was used to determine the location of the peak with sub-sample precision. The resulting discrete-time measurements of displacement d[z,m], a function both of target range z and echo index m were converted to a velocity estimate v[z,m] by the finite difference approximation where PRF is the tracking pulse v[z,m]=(d[z,m+1]−d[z,m])·PRF, repetition frequency. In the case of SMURF echo sequences, the tracking process results in a single two dimensional matrix v of velocity estimates vs. depth and time. The modified-SMURF pulse sequences are tracked identically but split into two matricies, $v_1$ and $v_2$, corresponding to velocity estimates associated with the first and second pushing pulses.

The method used to generate modulus estimates varied slightly depending on the pulse sequence used. For SMURF sequences the autocorrelation method described in "Validation of SMURF estimation of shear modulus in hydrogels" (supra) was used. The velocity sample was upsampled by a factor of ten by low-pass interpolation to improve the precision of the shear wave delay estimates. For each depth z the autocorrelation R of the upsampled discrete time velocity estimate $v_z[n]$ was calculated as $$R_v[m] = \sum_n v[z,n]v[z,n+m]. \tag{5}$$

The lag corresponding to the period of the vibration signal at depth z was taken to be the lag of the peak of $R_{v_z}[m]$ in the range $m_{min} < m < \infty$, where $m_{min}$ is the lag of the minimum $R_{v,v}$ for a given z. Identification of this peak was improved by suppression of low-frequency components of the velocity signal (due either to transducer motion or the low-frequency, non-spatially modulated component of the velocity signal[12]) by subtracting a second order polynomial fit from the autocorrelation of the velocity signal at each depth. The frequency f of the SMURF-induced shear wave is taken to be the reciprocal of the lag of the identified local maximum of R. The shear modulus G was then calculated as $$G = \rho(\Delta_p f)^2 \frac{1}{(1-fT)^2}, \quad (6)$$

where T is the time between push pulses, and $\rho$ the material density (assumed to be 1.0 g/cm$^3$). The factor of $1/(1-fT)^2$ is a correction term arising from the propagation of the shear wave due to the first pushing pulse before the transmission of the second pulse. This early propagation increases the effective spacing between beams.

Processing of the SMURF-mod data is similar in principle. Cross-correlation of the velocity signals $v_1$ and $v_2$ at each depth z was used to determine the difference in arrival time $\tau$ due to the extra distance $\Delta_p$ the shear wave due to the second push pulse must propagate to arrive at the tracking location. Cross correlation was calculated as $$C_{v_1,v_2}[m] = \sum_n v_1[z,n]v_2[z,n+m]. \quad (7)$$

The lag M (in samples) of global maximum of $C_{v1,v2}[m]$ was taken as the arrival time difference between the two shear waves. Dividing this sample lag by the pulse repetition frequency yields the time difference $\tau$. The shear wave speed $c_s$ is taken to be the ratio and $\Delta_p/\tau$, and the modulus obtained through the relation $$G = \rho c_s^2. \quad (8)$$

Note that, in contrast to the SMURF calculation, no correction factor is applied. The velocity signals $v_1[z,n]$ and $v_2[z,n]$ have their temporal origin set with respect to their corresponding pushing pulses; no time difference would be observed in the case where $\Delta_p = 0$.

For both pulse sequences the shear wave propagation paths are identical except for the difference $\Delta_p$. The estimated modulus thus corresponds to the modulus of the region between the pushing pulses. Because the tracking of the tissue takes place along the same A-line in all cases, any decorrelation or speckle-induced noise is identical for both measurements. The differential nature of the time delay measurement ensures that biases common to both pulses are suppressed.

Similar to conventional B-mode imaging, multiple transmit foci were used to improve the depth of field of the image. Focal depths of 1.5, 2, 2.5 and 3 cm were used. The final image was a composite of the focal zones of each of these sub-images. In the results presented here, no blending of images from each focal zone was performed. The image sections were merely stacked together to form the composite image.

C. Phantoms

Three phantom types were used in this study. Homogeneous phantoms, with uniform shear modulus, acoustic wavespeed, attenuation, and backscatter characteristics, were used to verify the calibration of the imaging sequences. A phantom containing spherical lesions of varying shear modulus was used to evaluate the effect of contrast on shear modulus images. Last, a phantom with a conical inclusion was scanned to asses the spatial resolution of the imaging sequences.

Homogeneous Phantoms

Two cylinders of Zerdine tissue-mimicking material (Computerized Imaging Reference Systems, Inc, Norfolk, Va.) were used as homogeneous phantoms. The cylinders had a diameter of 5.1 cm and a height of 2.4 cm. The nominal sound speed and attenuation were 1540 m/s and 0.5 dB/cm/MHz, respectively. The shear modulus of the compliant (G=5.5 kPa) and stiff (G=12 kPa) cylinders determined through unconfined compression was taken as the gold-standard value. (Stephen McAleavey, Erin Collins, Johanna Kelly, Etana Elegbe, and Manoj Menon, "Validation of smurf estimation of shear modulus in hydrogels," Ultrasonic Imaging, 31:111-130, 2009.)

Spherical Inclusion Phantom

A CIRS Model 049 Elastography Phantom was used as a test target for imaging (Computerized Imaging Reference Systems, Inc, Norfolk, Va.). This phantom is ultrasonically tissue mimicking with a sound speed of 1540 m/s and attenuation of 0.5 dB/cm/MHz. The phantom contains spherical inclusions that appear iso-echoic with respect to the background in B-mode but differ significantly in shear modulus. The nominal moduli, as specified by the manufacturer, of the background and scanned inclusions are listed in Table 1. Spheres 1 cm in diameter, centered 2.5 cm below the scanning surface, were imaged. Each sphere was scanned individually, as the field of view was insufficient to include multiple lesions. Scans of the phantom were performed with the scan plane aligned with the diameter of the spherical inclusions.

TABLE 1

Nominal shear moduli of scanned components of CIRS Model 049 phantom.

| Material | Shear Modulus (kPa) |
| --- | --- |
| Background | 8.3 ± 1.3 |
| Type I Lesion | 2.7 ± 1 |
| Type II Lesion | 4.7 ± 1.3 |
| Type III Lesion | 15 ± 1.7 |

Conical Inclusion Phantom

Figure 12A:
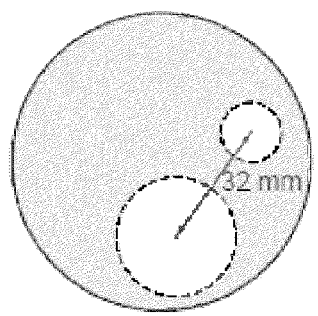
FIGS. 12A-12B are diagrams of a cone phantom, wherein the shaded areas represent the background, and the non-shaded areas indicate the inclusions.
Figure 12B:
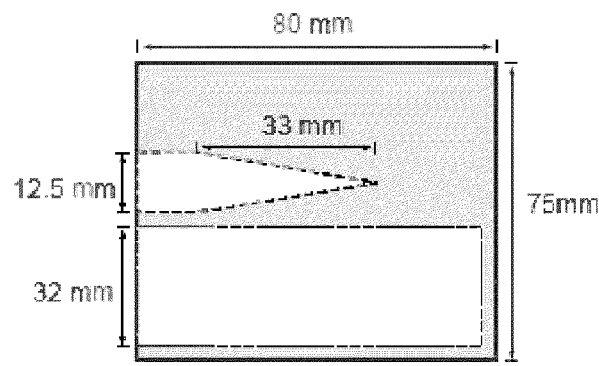

To ascertain the effect of lesion diameter on modulus estimate, a conical phantom was fabricated. This phantom, sketched in FIGS. 12A-12B, contained conical and cylindrical inclusions of low shear modulus in a relatively stiffer background. The conical section has a height of 33 mm and base diameter 12 mm. The phantom was gelatin based and used cornstarch as a scattering agent.

Circular cross sectional scans of the conical inclusion were obtained at nine locations in 4 mm increments along the axis of the cone. Translation of the transducer was performed by a linear stage. The phantom was acoustically coupled to the transducer through a mineral oil at a separation of 1-2 mm. The base of the cone was taken as the zero point for scan plane translation along the axis of the cone. Alignment of the scan plane with the base was achieved by inspection of B-mode images; the scan plane which just included a clear specular reflection from the cylindrical base of the conical section was taken as the starting scan plane. Longitudinal scans of the conical section were obtained with the cone axis aligned within the scan plane.

D. Porcine Liver

Porcine liver tissue was obtained fresh at slaughter from a local butcher. The liver was kept immersed in chilled 0.9% saline until scanning. A single lobe of the liver was excised from the whole and kept immersed in saline for scanning. The chilled saline was replaced with room temperature saline, and the liver allowed to warm for 30 minutes. The liver was scanned to find a plane with uniform B-mode appearance, free from obvious large vessels, and SMURF data collected. A stiff lesion was then induced by injection of 0.5 mL of 10% gluteraldehyde solution. Shear modulus images were obtained at four and eight minutes after the injection.

Results

Homogeneous Phantom

Shear modulus images of the uniform Zerdine phantoms are presented in FIGS. 6A-6F. These images have not been subjected to any median or spatial average filtering. The mean and standard deviation of the modulus estimate over the field of view for each phantom is listed in Table 2. The mean modulus values agree within the associated standard deviation across each of the beam sequences. No bias in the modulus estimate appears to be introduced by the use of the second-order fit autocorrelation filtering of the SMURF data. The filtering does eliminate some false-peak detection errors that lead to gross underestimates of the modulus, as seen in unfiltered modulus estimates in FIGS. 6A-6H. Sample auto- and cross-correlation traces for each method are shown in FIGS. 8A-8D.

TABLE 2

Modulus data for uniform phantoms.

| | MTS | SMURF (none) | SMURF (filtered) | SMURF-mod |
|---|---|---|---|---|
| Compliant | 5.1 | 5.51 (0.66) | 5.59 (0.19) | 5.73 (0.18) |
| Stiff | 12.4 | 13.8 (1.8) | 13.7 (0.86) | 12.9 (0.32) |

Values given are the mean shear modulus values (in kilopascals) over the field of view in FIGS. 6A-6H.
Values in parenthesis are the sample standard deviation of the estimates over the field of view.

Spherical Inclusion Phantom

Matched B-mode, SMURF, and SMURF-mod images of Type I, II, and III spherical inclusions are shown in FIGS. 7A-7I. Modulus values for the lesions are consistent for both estimators. The horizontal band of slightly lower modulus is thought to be a seam (visible in the matched B-mode images) in the phantom introduced in the manufacturing process. The low-modulus artifact in the lower-right quadrant of the SMURF image of Type III lesion is a failure of the autocorrelation estimator. In this region a "false peak" in the autocorrelation with greater lag than the correct value has been identified. This artifact illustrates an advantage of the SMURF-mod method, namely freedom from false-peak errors of this type.

Using the SMURF-mod sequence, it is possible to use a smaller value of $\Delta_P$ and still distinguish resulting two shear waves peaks, due to their greater separation in time. This fact leads naturally to the question of whether lateral resolution can be enhanced by closer spacing of push beams of a given size. To address this question, a series of images were formed with varying push beam spacing, shown in FIGS. 9A-9F. Modulus estimates are consistent across all push beam spacings but show increased noise with decreasing beam spacing. An increase in measurement variance is expected with decreasing beam spacing, as a given error in the arrival time difference τ becomes a greater fraction of the time difference. While a slight sharpening of the lateral edges is evident, the sharpening is not as large as would be suggested by the reduction in $\Delta_P$. A possible explanation for the modest enhancement in resolution with reduced push beam spacing is the width of the pushing beams, which remained unchanged as the beams were moved together. At the focus the distance between the lateral nulls of the intensity pattern is 2.48 mm. Thus, as the beam spacing is reduced from this value, the beam overlap becomes significant. Furthermore, the variance in the estimate increases, as the uncertainty in the arrival times becomes a larger fraction of the difference in arrival times.

Gelatin Phantom

Modulus images of cross sections through the gelatin phantom are presented in FIG. 10A-10H. The diameter in the scan plane varies from 12 to 1.5 mm in the images shown. The modulus estimates at the center of the lesion remain consistent except for the smallest lesions, when blurring with the background results in elevated values. The asymmetry of the smaller diameter sections is due to the anisotropic resolution of this method. The lateral resolution is strongly determined by the push beam width and spacing, while axial resolution is primarily dependent on the tracking pulse length and tracking window size. In the present case the push beam spacing is 2.48 mm while the tracking pulse and window together are 1.2 mm, implying a 2-1 resolution asymmetry.

An apparent shear modulus variation is visible between 20 and 30 mm depth radiating downward from the left and right edges of the inclusion. This is due to refraction of the push-beam by the ultrasound wave speed differences in the two regions. Pulse echo measurements subsequent to the SMURF scans of this phantom indicated longitudinal wave speeds of 1590 m/s in the background and 1640 m/s in the conical section. This is considered in the discussion section.

Matched B-mode and modulus images of the cone phantom with the scan plane aligned with the cone axis is shown in FIG. 4A-4C. Both the raw estimate and estimate with a 1 mm×1 mm spatial median filter and 2× spatial interpolation are presented for comparison.

Liver

Matched B-mode and SMURF-mod images of porcine liver tissue are shown in FIGS. 11A-11F. Prior to injection of gluteraldehyde the modulus images are relatively uniform with an average estimated shear modulus of 3 kPa. Four minutes after injection of 0.5 mL 10% glutaraldehyde a stiff lesion, approximately 4 mm in diameter, is clearly visible in the modulus image. A more modest increase in stiffness is visible over a larger area surrounding the injection site. This larger region shows greater stiffness eight minutes after injection. The B-mode images are essentially unchanged over the course of the experiment.

Standard SMURF images are not shown, as the method failed in liver tissue. While displacement images showed that both push beams displaced the liver tissue, the initially distinct peaks in displacement merged into a single, broader peak before any significant shear wave propagation occurred. Thus attenuated, the spatially modulated component was too small to be detected successfully at adjacent tracking locations. As the SMURF-mod results suggest, increasing the spacing between pushing beams would allow for distinguishable spatial modulation peaks to be detected, but at the cost of lateral resolution.

Discussion

The homogeneous elastic phantom results indicate that both SMURF methods yield comparable modulus estimates.

As expected, the resolution of both SMURF and SMURF-mod is similar, based on images of the spherical inclusion phantom. Identical push-beam spacing was used for both methods, and dispersion was negligible. Under these conditions both sequences produce similar results. The SMURF-mod sequence simplifies somewhat the signal processing needed to reconstruct a modulus image. The increased temporal separation makes it easier to time the arrival of the two shear waves and avoid the false autocorrelation peak possible with SMURF. As demonstrated here, however, false peaks can be effectively eliminated by high-pass filtering of the autocorrelation signal. Because of the extra time required to collect the SMURF-mod ensemble, sensitivity to physiological and transducer motion can be expected to increase, and the maximum frame rate adversely affected.

Where the two methods differ significantly in performance is in viscoelastic media. Here the SMURF-mod sequence is superior. Dispersion rapidly attenuated the high-frequency, spatially modulated component of the shear wave generated by the SMURF sequence, rendering it undetectable. While an increased push beam spacing would lower the induced shear wave frequency and allow detection, this would also adversely affect lateral resolution. Introduction of the time delay between push beams in the SMURF-mod sequence allowed for successful timing of shear wave propagation. The advantages of tracking at a single location are retained in the SMURF-mod sequence.

In FIGS. 10A-10H an image artifact is visible distal to the left and right edges of the circular inclusion. This artifact is visible as lines of low apparent shear modulus relative to the background. These lines are due to the difference in the longitudinal (ultrasound) wave speed between the inclusion and background. While sound speed error in the inclusion causes a refraction of all the beams, it is significant in the modulus reconstruction only to the degree that it causes a change in the effective push-beam spacing $\Delta_P$. Refraction of the tracking beam (unless extreme) affects the shear wave signals from both push beams equally and does not bias the result. Refraction-induced variation in $\Delta_P$, on the other had, leads to an underestimate of modulus if the beams refracted such that $\Delta_P$ is increased leads to an underestimate of the true shear modulus. While undesirable, this artifact would also exist in methods that track the propagation of a single shear wave at multiple locations, and is not inherent to SMURF. A related concern is that variations in the tissue absorption and scattering, along with the separate propagation paths of the push beams, may induce shear modulus measurement variance. While the literature indicates that absorption is the dominant mechanism of attenuation in liver and thus one might expect radiation force to be likewise determined primarily by tissue absorption properties, we have not demonstrated this here. (K. J. Parker, "Ultrasonic attenuation and absorption in liver tissue," Ultrasound in Medicine and Biology, 9(4):363-369, 1983.)

Exemplary Imaging Discussion

The echo from a collection of scatterers in two dimensions can be modeled as $$r(t) = \int\int_{-\infty}^{\infty} h(x,z,t)\gamma(x,z)dxdz \qquad (9)$$

where h(x,z,t) is the pulse-echo response to a point scatterer at (x,z), and γ(x,z) is the object function, which describes the scattering properties as a function of position (R. J. Zemp, C. K. Abbey, M. F. Insana, "Linear System Models for Ultrasonic Imaging: Application to Signal Statistics of Imaging," IEEE Transactions on Ultrasonics, Ferroelectrics and Frequency Control, Vol 18, pp. 318-329, 2003). Here the scatterers are taken to be in the xz plane; ultrasound propagation is in the +z direction.

While h(x,z,t) is spatially varying in general, local spatial invariance may be assumed and the impulse response modeled as $$h(x,z,t)=h_e(x,t-2z/c)e^{j\omega_l(t-2z/c_l)} \qquad (10)$$

where $h_e$ is a slowly varying (compared to the ultrasound wavelength) envelope function, $\omega_l$ the ultrasound radian frequency, and $c_l$ the acoustic wave speed. This model implies that target displacements in the ±z direction induce a proportional change in echo arrival time but do not otherwise change the echo.

A solid elastic target will support shear waves, in addition to the longitudinal ultrasound waves. Such a shear wave in the target object can serve to displace scattering centers. A z-polarized plane shear wave of frequency $\omega_s$ propagating in the +x direction induces a displacement of the scatterers in the ±z direction of $$d_z=a \cos(\omega_s\tau-k_sx) \qquad (11)$$

where a is the displacement amplitude, τ is time, and $k_s$ the wavenumber of the shear wave. The passage of the shear wave moves a point at z to position z+$d_z$. By a change of variable, and assuming that a displacement of ±a results in a negligible change in the value of $h_e$, Equation 9 can be written to include the effect of the shear wave as $$r(t, \tau, k_s) = \int_{-\infty}^{\infty} \hat{\gamma}(x, t)e^{j\beta\cos(\omega_s\tau-k_sx)}dx \qquad (12)$$

where $\beta = 2a\omega_l/c_l$ $$\hat{\gamma}(x, t) = \int_{-\infty}^{\infty} h_e(x, t-2z/c)e^{j\omega_l(t-2z/c_l)}\gamma(x, z)dz \qquad (13)$$

$\hat{\gamma}(x,t)$ represents the object function convolved in the z direction with the impulse response, and shaded in the x direction by $h_e$. That is, $\hat{\gamma}$ is the object function blurred in the range direction and illuminated but unblurred in the lateral direction. r(t, τ; $k_s$) represents the compete echo as a function of time, modulated by the shear wave displacement of the scatterers. The time variables for the RF echo (t) and the shear wave (τ) are separated with the assumption that the shear wave period is much greater than the interaction time of the RF pulse with the scatterers. That is, $d_z$ may be treated as a constant during the interaction of the RF pulse with the target. In the absence of any shear wave induced motion equations 9 and 13 are equivalent.

Equation 13 is a phase-modulated version of Equation 9. For small values of β, i.e. |β|<<π, $e^{j\beta \cos(\omega t-kx)} \approx 1+j\beta \cos(\omega t-kx)$. Using this approximation and the identity cos(x-π/2)=sin(x) we can write $$r(t, 0, k) - r(r, \pi/\omega, k) = 2j\beta \int_{-\infty}^{\infty} \hat{\gamma}(x)\cos(kx)dx \qquad (14)$$

and $$r(t, -\pi/2\omega, k) - r(t, \pi/2\omega, k) = -2j\beta \int_{-\infty}^{\infty} \hat{\gamma}(x)\sin(kx)dx \qquad (15)$$

Let $I(t, k) = r(t, 0, k) - r(t, -\pi/\omega, k)$ and $Q(t, k) = r(t, -\pi/2\omega, k) - r(t, \pi/2\pi, k)$. (Note, neither I nor Q are necessarily real). Then $$I(t, k) + jQ(t, k) = 2j\beta \int_{-\infty}^{\infty} \hat{\gamma}(x, t)e^{-jkx} dx \quad (16)$$

that is, the sum $I(k)+jQ(k)$ is Fourier Transform of $\hat{\gamma}(x, t)$ scaled by $2j\beta$. The inverse Fourier transform may be applied, then, to recover $\hat{A}(x)$ from the signals $I(k)$ and $Q(k)$, $$\hat{\gamma}(x, t) = \frac{1}{4\pi j \beta} \int_{-\infty}^{+\infty} (I(k) + jQ(k))e^{jkx} dk \quad (17)$$

Recovery of $\hat{\gamma}$, then, yields an image of the object $\gamma$ blurred by the axial (time) component of the impulse response, and shaded laterally by the extent of $h_e$. The x component of the spatial resolution of $\gamma$ is limited only by the range of $k_s$ values that may be applied to the target.

Methods

A. Simulation

Point Targets: Point targets subject to plane shear wave vibration in a uniform, lossless elastic medium were modeled using Field II (J. A. Jensen, "Field: A Program for Simulating Ultrasound Systems," Medical and Biological Engineering and Computing, Vol 34, pp. 351-352, 1996). Key parameters are listed in Table 3. These parameters were chosen in part to match the phantom experiments described in Part III-B. A single element transducer, comparable to a single element of a 6 MHz array (0.2 mm wide), was modeled as the source and receiver. Shear wave propagation was modeled as a plane wave over the frequencies listed. Scatterers were translated according to Equation 11 and echoes calculated at shear wave phases of −90, 0, 90 and 180 degrees, i.e. $\tau = \pi/2\omega$, 0, $\pi/2\omega$, and $\pi/\omega$. Intermediate signals $I(t, k)$ and $Q(t, k)$ were calculated as described previously, and a 1D inverse FFT applied along the $k_s$ direction to generate the images. Zero-padding of $k_s$ domain data was used to achieve interpolation in the image domain.

TABLE 3

Shear wave modulated imaging simulation parameters

| | |
|---|---|
| $c_s$, background | 2.2 m/s |
| $c_s$, lesion | 2.2 or 2.74 |
| $f_0$ | 6.67 MHz |
| $f_s$ | 50-1500 Hz, 50 Hz steps |
| a | 7 μm |

2) Diffuse target: A 1 cm diameter hyperechoic lesion in a 2×2 cm block was modeled using Field II. The block had a shear modulus G of 5 kPa, while the lesion was modeled as either G=5 or G=7.5 kPa. Comsol Multiphysics finite element software was used to calculate the propagation of shear waves from left to right in the model, assuming free boundaries for the top and bottom. A matched lossy layer was added on the right hand side (not shown) to eliminate reverberations of the shear wave. The deformations calculated by the finite element simulation at each of the four phases of the shear wave were applied to the scatterers in Field II simulation. Echoes were calculated and the image reconstructed as for the point target simulations.

B. Experiment

Gelatin block phantoms containing nylon monofilament "wire" targets were imaged using the setup described below. The blocks were 10×4×6.5 cm (x,y,z) in size and composed of 7.5% gelatin by weight. Lengths of nylon monofilament (0.13 mm diameter) were embedded in the gelatin block parallel to the y-axis, arranged along the diagonal of a 2.5 mm (0.1") square grid. The shear modulus of the phantom was determined by unconfined compression testing to be approximately 5 kPa. A second gelatin block phantom contained a 6 mm diameter hyperechoic cylindrical inclusion in lieu of the monofilament targets. This inclusion was made of the same gelatin concentration as the rest of the phantom, but included powdered cellulose particles as an ultrasound scattering agent.

Figure 13:
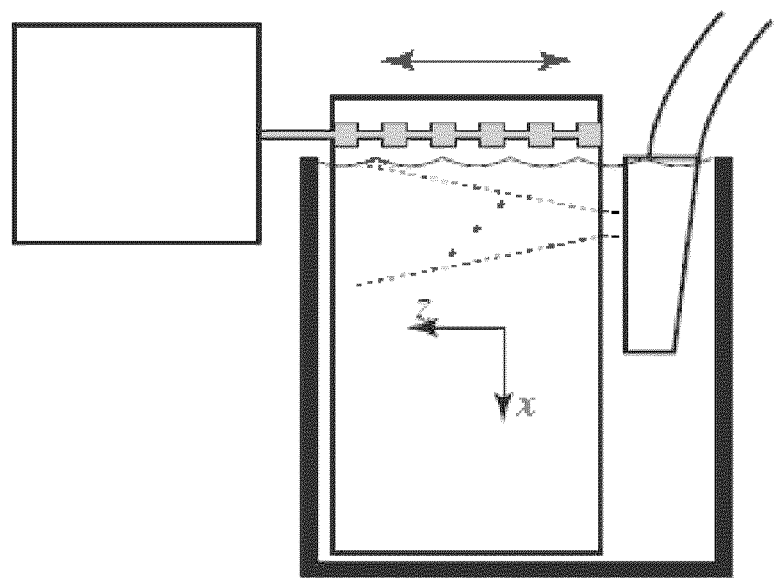
FIG. 13 is a diagram showing the physical relationship between key components of the experimental setup. The electromagnetic shaker (top left) induces a +x going shear wave. The nylon wire targets, indicated by the dots, are illuminated by an unfocused transducer element, which also receives the echo signals from all targets.
Figure 14:
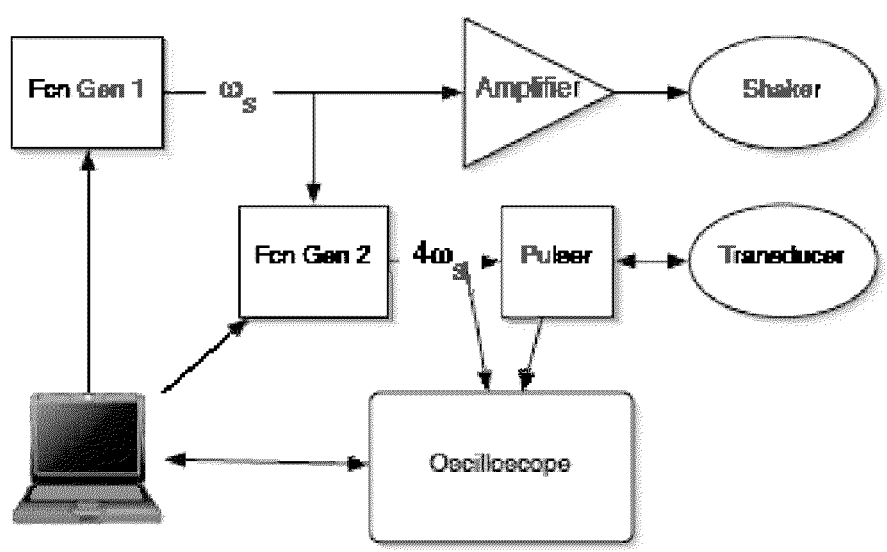
FIG. 14 is a block diagram representation of the signal flow for the data acquisition procedure described in the text.
Figure 15A:
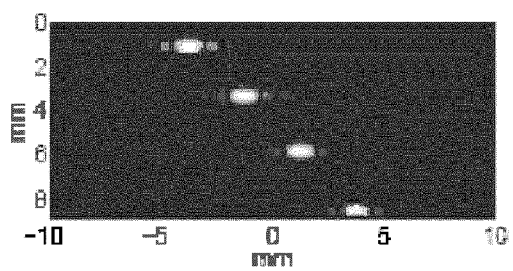
FIGS. 15A-15F: Left column 20 dB grayscale. Right column 40 dB grayscale. Top row: Boxcar (rect.) window applied. Center row: Hamming window applied. Bottom row: raised hamming window.
Figure 15B:
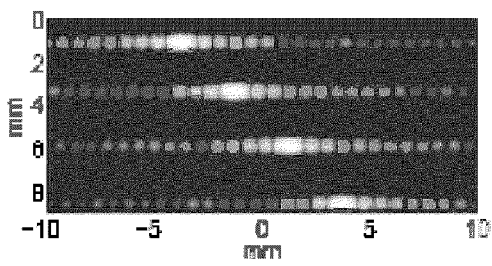
Figure 15C:
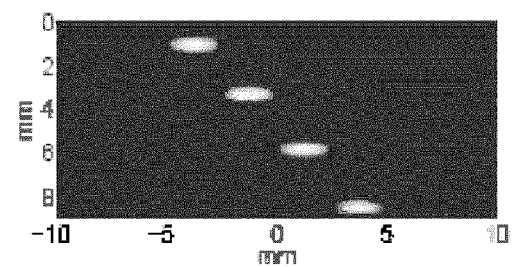
Figure 15D:
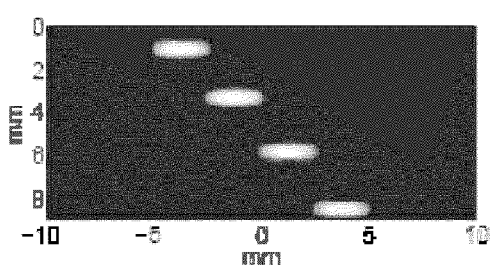
Figure 15E:
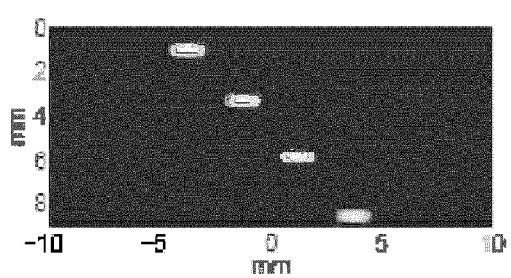
Figure 15F:
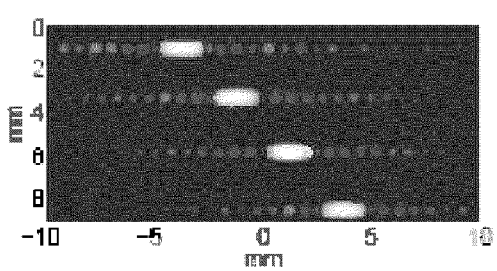

The experimental setup for imaging of the gelatin blocks is illustrated schematically in FIGS. 13 and 14. A digital function generator (Tektronix AFG3021B) drove an electromagnetic shaker (Bruel & Kjaer 4810) though a small amplifier (Bruel & Kjaer 2706). This function generator was synchronized to a second (Agilent 33220A) operating at four times the vibration frequency, allowing for echo acquisition at 0, 90, 180, and 270 degrees relative to the shear wave. This $4\omega_s$ signal triggered both the pulser/receiver and digital oscilloscope. Simultaneous acquisition of all four phases was necessary to avoid 1/f-like noise effects, due to building vibration, amplifier drift, etc.

Pulse-echo RF data were acquired using a single element of a 7 MHz linear array (Aloka) driven by a pulser-receiver (JSR DPR 300). A digital oscilloscope (LeCroy 44MXi) was used to record the echo signals. Echo averaging was used to improve SNR and the effective resolution of the oscilloscope. For each vibration frequency 1024 echoes were obtained, 256 for each phase. The echo ensemble average was calculated for each phase, and $I(k)$ and $Q(k)$ calculated as in equation as described previously. Note that since $I(t, k)=I(t, -k)$ and $Q(t, k)=-Q(t, -k)$, it is not necessary to generate −x going shear waves (i.e. waves with negative wavenumbers).

Results

FIGS. 15A-15F presents reconstructed images of simulated point targets. The lateral profile of the point targets demonstrate both the correct position of the wires. The lateral width of the wire images is determined by the range or bandwidth of the shear wave excitation; the greater the range, the tighter the lateral profile. In the simulation frequencies up to 1500 Hz are applied. Due to the truncation of the collected data in the frequency ($k_s$) domain, strong ringing artifacts are associated with the point response, as is most clearly visible in the 40 dB response. The application of Hamming and raised Hamming windows to the I and Q signals along the $k_s$ dimension is effective in controlling the sidelobe levels, with a consequent tradeoff in mainlobe width. Thus, mainlobe/sidelobe balance may be controlled just as apodization of the ultrasound aperture would be used conventionally.

Figure 16A:
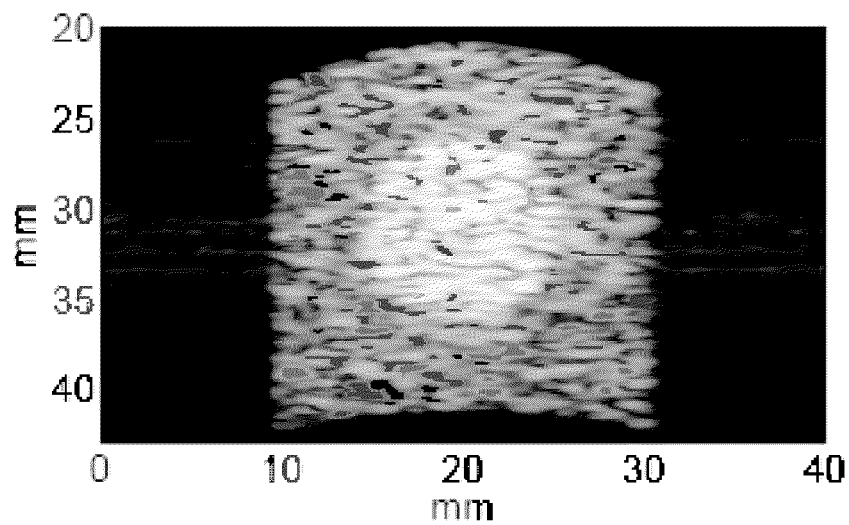
FIG. 16A is a simulated image of a 1 cm diameter lesion where the shear modulus of the lesion and the background are both 5 kPa. Image is on a 40 dB grayscale.
Figure 16B:
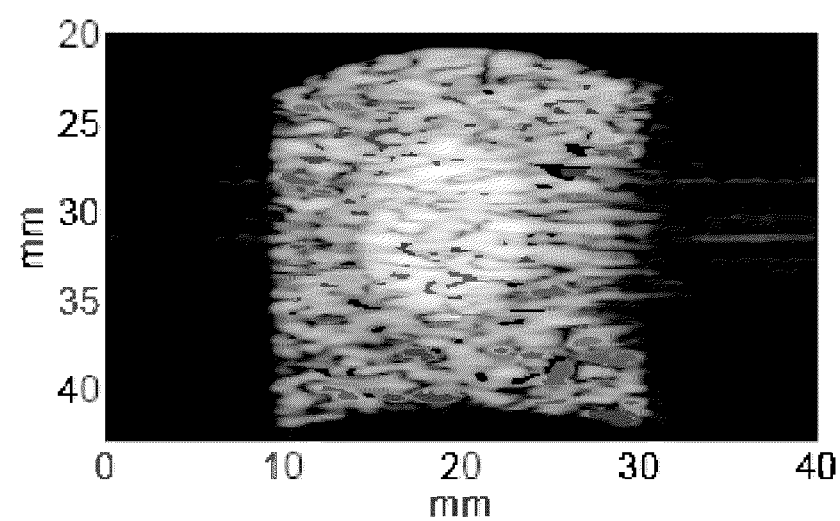
FIG. 16B is a simulated image of a 1 cm diameter lesion where the shear modulus of the lesion is 7.5 kPa and the shear modulus of the background is 5 kPa. Image is on a 40 dB grayscale.

Images of the hyperechoic lesion in the diffuse phantom are presented in FIGS. 16A-16B. No adjustment was made to the image to account for the distortion in the range direction due to time of flight differences between the center and lateral edges of the phantom; as a result the images exhibit some curvature of field. The image of the stiff lesion in a softer background is distorted laterally due to the greater shear wave velocity and consequent change in wavenumber.

Images of the wires in the gelatin phantom are shown in FIGS. 17A-17B, using the same dynamic ranges as for the simulated wires. The greater lateral blurring, especially evident in the 40 dB grayscale image, is due to deviations from ideal, constant amplitude planewave propagation in the phantom. While an adjustment was made for the expected decrease in shear wave amplitude with frequency due to attenuation and mass-loading of the shaker, additional, non-monotonic variations in shear wave amplitude with frequency were observed. This additional modulation leads to the observed distortion.

The reconstructed image of the 6 mm hyperechoic inclusion is shown in FIG. 18. The strong, broad echo at the top of the image is due to a small air bubble trapped at the interface between the cylinder and background. The circular profile of the target is visible and well-localized.

Discussion

The simulation and experimental results demonstrate the validity of the proposed method, insofar as a traveling plane shear wave to can be generated within the target. Lateral resolution is clearly due entirely to the shear-wave induced motion of the target, since in all cases a stationary, single element transducer is employed. One interesting observation is that, because lateral resolution does not depend on the phase of echoes at various points across the aperture (and in fact can be performed with a point source), the effects of an aberrating layer between the target and transducer are greatly reduced. While an aberrating layer may distort the overall illumination of the target, the image shape will remain relatively undistorted. A constant shift in the arrival time of an echo from a particular scatterer due to the aberrator will not distort the lateral position estimate in this method. A possible application is to aid B-mode imaging by using the method to enhance the lateral resolution of a conventionally focused beam.

The development presented in Part II assumed a small amplitude shear wave, such that higher order terms of the expansion of the modulation exponential were negligible. While the approximation is valid for the experiments presented here, it is not required. The use of higher-amplitude shear waves, for which higher order terms of the expansion are significant, may allow greater resolution. Higher order terms induced phase modulation components at integer multiples of the shear wave frequency, and corresponding integer multiples of the wavenumber. The tradeoff between effects of shear wave attenuation and feasibility of large amplitude vibration generation are non-obvious.

The most significant limitation of the proposed method is the ability to generate shear waves of a known wavelength in tissue. Challenges here include the large variation in shear modulus of the various tissues of the body, and the frequently strong viscoelastic component. The strong attenuation of shear waves with increasing frequency makes it infeasible to propagate them over large distances. These limitations might be addressed by using acoustic radiation force to generate shear waves close to the region of interest.

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:

1. A method of determining the shear modulus of a tissue of an individual, the method comprising the steps of:
   (a) transmitting at least one acoustic pulse at a first location of the individual and receiving a reference echo signal resulting from the at least one acoustic pulse;
   (b) transmitting a first push pulse at a second location of the individual;
   (c) transmitting a second push pulse that has a temporally distinct spatial peak from the first push pulse at a third location of the individual, wherein the first location, second location, and third location are each spatially distinct;
   (d) transmitting a series of tracking pulses at the first location and receiving a tracking echo signal from each tracking pulse;
   (e) determining the effect of the first and second push pulses on the tissue of the individual at the first location by analyzing the tracking echo signals; and
   (f) calculating the shear modulus of the tissue of the individual based on the effect of the first and second push pulses on the tissue of the first location compared to the reference echo signal.

2. The method of claim 1, wherein the effect of the first and second push pulses on the tissue is displacement of the tissue.

3. The method of claim 1, wherein the at least one acoustic pulse and the tracking pulses are B-mode ultrasound pulses.

4. The method of claim 1, wherein the first and second push pulses comprise a 200 cycle toneburst having a center frequency of 4.21 MHz.

5. The method of claim 1, wherein the second location and the third location are located on a same side of the first location.

6. The method of claim 1, wherein the distance between the second location and the third location of the individual ($\Delta P$) is selected such that a first lateral null of the first push pulse aligns with a first lateral null of the second push pulse.

7. The method of claim 1, wherein a time between the first and second push pulses is 134 µs, the distance between the second location and the third location ($\Delta P$) is 2.48 mm, and the distance between the first location and the second location ($\Delta T$) is 1.8 mm.

8. The method of claim 1, wherein transmitting the at least one acoustic pulse at the first location of the individual and receiving the reference echo signal comprises transmitting two acoustic pulses and receiving two reference echo signals.

9. A method of determining the shear modulus of a tissue of an individual using acoustic pulses, the method comprising the steps of:
   (a) transmitting at least one acoustic pulse at a first location of the individual and receiving a reference echo signal resulting from the at least one acoustic pulse;
   (b) transmitting a first push pulse at a second location of the individual;
   (c) transmitting a first series of tracking pulses at the first location and receiving a first set of tracking echo signals, wherein each tracking echo signal of the first set is received as a result of each tracking pulse of the first series;
   (d) determining the effect of the first push pulse on the tissue of the individual at the first location by analyzing the first set of tracking echo signals;
   (e) transmitting a second push pulse that has a temporally distinct spatial peak from the first push pulse at a third location of the individual, wherein the first location, second location, and third location are each spatially distinct;
   (f) transmitting a second series of tracking pulses at the first location and receiving second set of tracking echo signals, wherein each tracking echo signal of the second set is received as a result of each tracking pulse of the second series;
   (g) determining the effect of the second push pulse on the tissue of the individual at the first location by analyzing the second set of tracking echo signals; and (h) calculating the shear modulus of the tissue of the individual based on the effect of the first and second push pulses on the tissue of the first location compared to the reference echo signal.

10. The method of claim 1, wherein the at least one acoustic pulse and the tracking pulses are B-mode ultrasound pulses.

11. The method of claim 1, wherein the first and second push pulses comprise a 200 cycle toneburst having a center frequency of 4.21 MHz.

12. The method of claim 1, wherein the second location and the third location are located on a same side of the first location.

13. The method of claim 1, wherein the distance between the second location and the third location of the individual ($\Delta P$) is selected such that a first lateral null of the first push pulse aligns with a first lateral null of the second push pulse.

14. The method of claim 1, wherein a time between the first and second push pulses is 134 µs, the distance between the second location and the third location ($\Delta P$) is 2.48 mm, and the distance between the first location and the second location ($\Delta T$) is 1.8 mm.

15. The method of claim 1, wherein the first series of tracking pulses comprises 30 tracking pulses.

16. The method of claim 1, wherein the second series of tracking pulses comprises 40 tracking pulses.

17. A system for producing an image of a region of tissue of an individual, the system comprising:
   an ultrasonic transducer for transmitting acoustic pulses and receiving echo data, the ultrasonic transducer having an addressable array of ultrasonic elements;
   a controller in communication with the ultrasonic transducer and programmed to:
   (a) cause a first set of ultrasonic elements of the ultrasonic transducer to transmit and receive an ensemble of acoustic pulses and corresponding echo signals, the ensemble of acoustic pulses comprising:
   (i) at least one acoustic pulse transmitted at a first location of the individual and reference echo signal received at the first location;
   (ii) a first push pulse transmitted at a second location of the individual;
   (iii) a second push pulse that has a temporally distinct spatial peak from the first push pulse transmitted at a third location of the individual, wherein the first location, the second location, and the third location are each spatially distinct; and
   (iv) a series of tracking pulses transmitted at the first location and echo signals received at the first location from each tracking pulse to determine the effects of the first and second push pulses on tissues of the individual at the first location;
   (b) calculate a shear modulus of each tissue of a first set of tissues of the individual based on the received echo signals resulting from the ensemble;
   (c) repeat steps (a) and (b) for different sets of ultrasonic elements of the ultrasonic transducer than the first set until a predetermined number of ultrasonic elements have transmitted the ensemble; and
   (d) generate an image of the tissue by compiling at least the shear modulus of each tissue of each echo signal set as a pixel value of the image.

18. The system of claim 17, wherein the series of tracking pulses comprises:
   a first series of tracking pulses transmitted at the first location and echo signals received at the first location from each tracking pulse of the first series to determine the effects of the first push pulse on tissues of the individual at the first location; and
   a second series of tracking pulses transmitted at the first location and echo signals received at the first location from each tracking pulse of the second series to determine the effects of the second push pulse on the tissue of the first location.

* * * * *

UNITED STATES PATENT AND TRADEMARK OFFICE
CERTIFICATE OF CORRECTION

PATENT NO. : 8,753,277 B2  
APPLICATION NO. : 12/965807  
DATED : June 17, 2014  
INVENTOR(S) : McAleavey Page 1 of 1

It is certified that error appears in the above-identified patent and that said Letters Patent is hereby corrected as shown below:

In the Claims

Column 23, line 5, Claim 10, "claim 1" should read --claim 9--;

Column 23, line 7, Claim 11, "claim 1" should read --claim 9--;

Column 23, line 10, Claim 12, "claim 1" should read --claim 9--;

Column 23, line 13, Claim 13, "claim 1" should read --claim 9--;

Column 23, line 17, Claim 14, "claim 1" should read --claim 9--;

Column 23, line 22, Claim 15, "claim 1" should read --claim 9--; and

Column 23, line 24, Claim 16, "claim 1" should read --claim 9--.

Signed and Sealed this  
Second Day of December, 2014

Michelle K. Lee  
*Deputy Director of the United States Patent and Trademark Office*